(12) United States Patent
Motomura et al.

(10) Patent No.: US 10,981,877 B2
(45) Date of Patent: Apr. 20, 2021

(54) PRODUCTION METHOD FOR PYRAZOLE-AMIDE COMPOUND

(71) Applicant: Japan Tobacco Inc., Tokyo (JP)

(72) Inventors: Takahisa Motomura, Osaka (JP); Masafumi Inoue, Osaka (JP); Hirotsugu Ito, Osaka (JP); Takuya Matsuo, Osaka (JP); Koichi Suzawa, Osaka (JP); Hiroshi Yamamoto, Osaka (JP); Tsubasa Takeichi, Osaka (JP); Yasuyuki Kajimoto, Osaka (JP); Takashi Inaba, Osaka (JP); Takao Ito, Osaka (JP); Takahiro Yamasaki, Osaka (JP); Yukishige Ikemoto, Osaka (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/319,938

(22) PCT Filed: Jul. 28, 2017

(86) PCT No.: PCT/JP2017/027358
§ 371 (c)(1),
(2) Date: Aug. 27, 2019

(87) PCT Pub. No.: WO2018/021508
PCT Pub. Date: Feb. 1, 2018

(65) Prior Publication Data
US 2019/0375717 A1 Dec. 12, 2019

(30) Foreign Application Priority Data

Jul. 29, 2016 (JP) ................................ 2016-150657

(51) Int. Cl.
| | | |
|---|---|---|
| *C07D 231/12* | (2006.01) | |
| *C07C 45/64* | (2006.01) | |
| *C07C 43/23* | (2006.01) | |
| *B01J 23/44* | (2006.01) | |
| *B01J 31/02* | (2006.01) | |

(52) U.S. Cl.
CPC ............ *C07D 231/12* (2013.01); *B01J 23/44* (2013.01); *B01J 31/0231* (2013.01); *C07C 43/23* (2013.01); *C07C 45/64* (2013.01)

(58) Field of Classification Search
None
See application file for complete search history.

(56) References Cited

U.S. PATENT DOCUMENTS

| | | | |
|---|---|---|---|
| 7,098,241 B2 | 8/2006 | Grossmann et al. | |
| 7,485,634 B2 | 2/2009 | Martin et al. | |
| 7,585,837 B2 | 9/2009 | Shechter et al. | |
| 7,674,795 B2 | 3/2010 | Mailliet et al. | |
| 8,133,992 B2 | 3/2012 | Martin et al. | |
| 8,343,910 B2 | 1/2013 | Shechter et al. | |
| 8,343,994 B2 | 1/2013 | Motomura et al. | |
| 8,735,350 B2 | 5/2014 | Shechter et al. | |
| 8,871,934 B2 | 10/2014 | Motomura et al. | |
| 8,877,709 B2 | 11/2014 | Shechter et al. | |
| 8,957,094 B2 | 2/2015 | Yoshida et al. | |
| 9,040,717 B2 * | 5/2015 | Motomura ............... | A61P 27/00 548/356.1 |
| 9,119,883 B2 | 9/2015 | Shechter et al. | |
| 9,433,683 B2 | 9/2016 | Shechter et al. | |
| 9,956,295 B2 | 5/2018 | Shechter et al. | |
| 2008/0200551 A1 | 8/2008 | Yamada et al. | |
| 2012/0035196 A1 | 2/2012 | Negoro et al. | |
| 2013/0190503 A1 | 7/2013 | Yoshida et al. | |

(Continued)

FOREIGN PATENT DOCUMENTS

| | | |
|---|---|---|
| RU | 2560168 C2 | 8/2015 |
| WO | 2003/011844 A2 | 2/2003 |

(Continued)

OTHER PUBLICATIONS

Aicher, T. et al., "(R)-3,3,3-Trifluoro-2-hydroxy-2-methyl-propionamides Are Orally Active Inhibitors of Pyruvate Dehydrogenase Kinase", Journal of Medicinal Chemistry, vol. 42, No. 15, pp. 2741-2746 (Jul. 1999).

Bebernitz, G.R. et al., "The Effect of 1,3-Diaryl-[1H]-pyrazole-4-acetamides on Glucose Utilization in ob/ob Mice", Journal of Medicinal Chemistry, vol. 44, No. 16, pp. 2601-2611 (Jul. 2001).

Horig, H. et al., "From bench to clinic and back: Perspective on the 1st IQPC Translational Research conference," Journal of Translational Medicine, vol. 2, No. 44, pp. 1-8 (Dec. 2004).

Karpov, V.M. et al., "Skeletal transformations of perfluoro-1-phenylindan under the action of antimony pentafluoride," Journal of Fluorine Chemistry, vol. 107, No. 1, pp. 53-57 (Nov. 2001).

(Continued)

*Primary Examiner* — Kamal A Saeed
(74) *Attorney, Agent, or Firm* — Venable LLP

(57) ABSTRACT

A production method of a compound represented by the formula [I]:

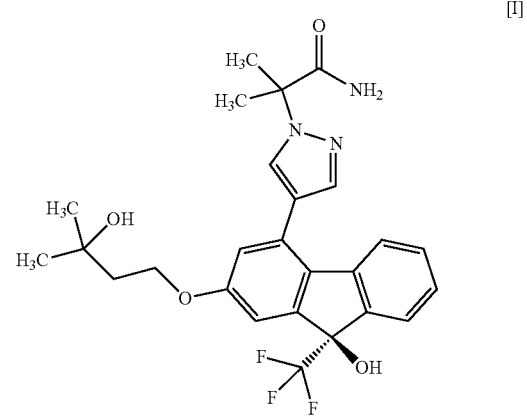

or a pharmaceutically acceptable salt thereof, or a hydrate thereof.

13 Claims, No Drawings

(56) References Cited

U.S. PATENT DOCUMENTS

| | | |
|---|---|---|
| 2014/0275523 A1 | 9/2014 | Angelaud et al. |
| 2014/0296316 A1 | 10/2014 | Motomura |
| 2015/0018403 A1 | 1/2015 | Motomura et al. |
| 2015/0025120 A1 | 1/2015 | Motomura et al. |
| 2015/0329491 A1 | 11/2015 | Motomura et al. |
| 2016/0074364 A1 | 3/2016 | Motomura et al. |
| 2018/0256547 A1 | 9/2018 | Motomura et al. |
| 2019/0177271 A1 | 6/2019 | Motomura et al. |
| 2020/0163937 A1 | 5/2020 | Motomura et al. |
| 2020/0308109 A1 | 10/2020 | Motomura et al. |

FOREIGN PATENT DOCUMENTS

| | | |
|---|---|---|
| WO | 2003/099821 A1 | 12/2003 |
| WO | 2004/089280 A2 | 10/2004 |
| WO | 2005/080322 A1 | 9/2005 |
| WO | 2006/123061 A2 | 11/2006 |
| WO | 2010/041748 A1 | 4/2010 |
| WO | 2010/123016 A1 | 10/2010 |
| WO | 2011/125836 A1 | 10/2011 |
| WO | 2014/142290 A1 | 9/2014 |
| WO | 2014/142291 A1 | 9/2014 |
| WO | 2015/002118 A1 | 1/2015 |
| WO | 2015/002119 A1 | 1/2015 |

OTHER PUBLICATIONS

Roche, T.E. et al., "Pyruvate dehydrogenase kinase regulatory mechanisms and inhibition in treating diabetes, heart ischemia, and cancer," Cellular and Molecular Life Sciences, vol. 64, pp. 830-849 (Feb. 2007).

International Search Report for PCT/JP2017/027358 (dated Oct. 24, 2017).

International Search Report for PCT/JP2014/056825 (dated Apr. 8, 2014).

Anissa Beladhria et al., "Pd-Catalysed Direct 5-Arylation of 1-Methylpyrazole with Aryl Bromides", Synthesis, 16, pp. 2553-2560 (Aug. 2011).

Extended European Search Report in European Application No. 17834510.4, dated Nov. 26, 2019 (9 pages).

\* cited by examiner

PRODUCTION METHOD FOR PYRAZOLE-AMIDE COMPOUND

TECHNICAL FIELD

The present invention relates to a novel production method of a pyrazole-amide compound or a salt thereof, or a hydrate thereof useful as an inhibitor of pyruvate dehydrogenase kinase (hereinafter to be abbreviated as PDHK), and an intermediate therefor.

SUMMARY OF THE INVENTION

The present invention aims to provide a novel production method of a pyrazole-amide compound or a salt thereof, or a hydrate thereof useful for the treatment or prophylaxis of diseases related to glucose metabolism disorder (e.g., diabetes (type 1 diabetes, type 2 diabetes etc.), insulin resistant syndrome, metabolic syndrome, hyperglycemia, hyperlactacidemia, diabetic complications (diabetic neuropathy, diabetic retinopathy, diabetic nephropathy, cataract etc.)), diseases in which supply of energy substrate to tissues is restricted (e.g., cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy), mitochondrial disease, mitochondrial encephalomyopathy, cancer, pulmonary hypertension and the like, and the like.

One embodiment of the present invention is as shown by the following [1] to [18a].

[1] A method for producing a compound represented by the formula [I]:

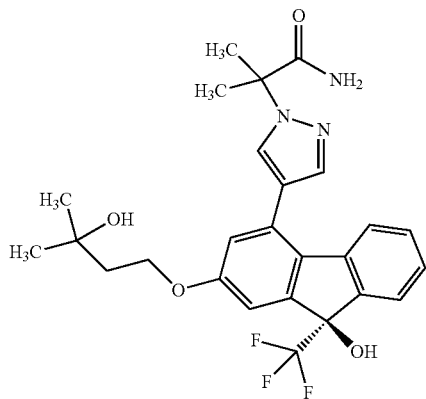

or a pharmaceutically acceptable salt thereof, or a hydrate thereof, wherein the method comprises a step of converting a compound represented by the formula [II]:

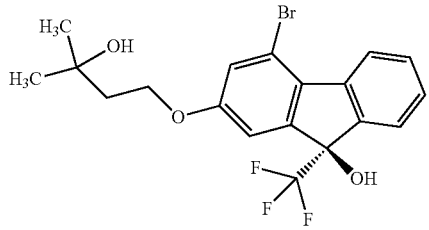

or a methanol solvate thereof to a compound represented by the formula [IV]:

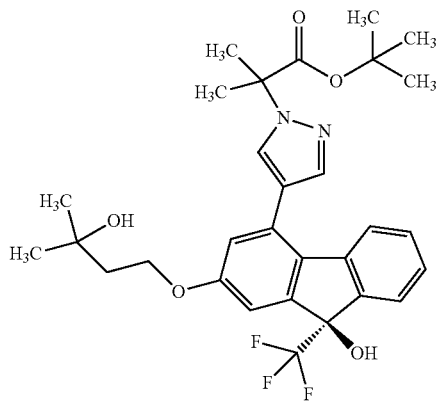

by a coupling reaction with a compound represented by the formula [III]:

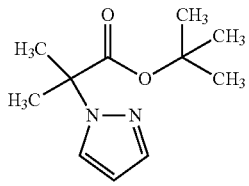

in the presence of a metal catalyst, a base and carboxylic acid.

[2] The method of the above-mentioned [1], wherein the metal catalyst is a palladium catalyst.

[3] The method of the above-mentioned [1] or [2], wherein the base is alkali metal carbonate or alkali metal acetate.

[4] The method of any of the above-mentioned [1] to [3], wherein the carboxylic acid is pivalic acid, isobutyric acid, propionic acid or benzoic acid.

[5] The method of any of the above-mentioned [1] to [4], wherein a reaction temperature of the coupling reaction is 80 to 150° C.

[6] The method of any of the above-mentioned [1] to [5], further comprising a step of hydrolyzing the compound of the aforementioned formula [IV] to convert same to a compound represented by the formula [V]:

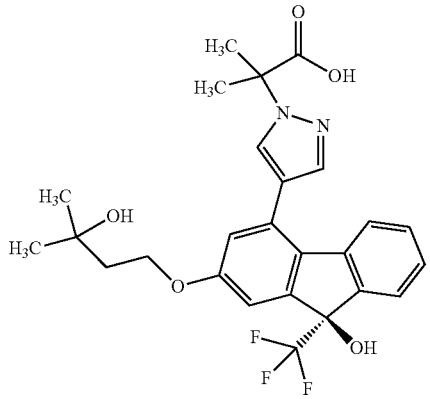

or a salt thereof.

[7] The method of the above-mentioned [6], further comprising a step of reacting the compound of the aforementioned formula [V] or a salt thereof with ammonia in the presence of a condensing agent to convert same to a compound represented by the aforementioned formula [I] or a pharmaceutically acceptable salt thereof, or a hydrate thereof.

[8] The method of any of the above-mentioned [1] to [7], wherein the compound of the aforementioned formula [II] is produced by a method comprising a step of reacting a compound represented by the formula [VI]:

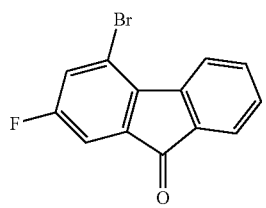

[VI]

with a compound represented by the formula [VII]:

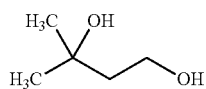

[VII]

in the presence of a base to convert same to a compound represented by the formula [VIII]:

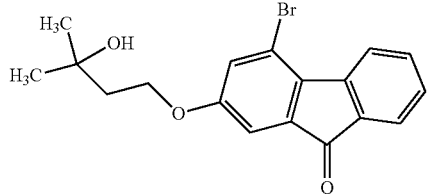

[VIII]

and a step of reacting the compound of the formula [VIII] with (trifluoromethyl)trimethylsilane in the presence of an asymmetric organocatalyst and then treating with an acid.

[9] The method of the above-mentioned [8], wherein the asymmetric organocatalyst is a cinchonidium salt.

[10] The method of the above-mentioned [9], wherein the cinchonidium salt is N-(4-tert-butyl-3-methoxybenzyl)cinchonidium bromide.

[10a] The method of the above-mentioned [9], wherein an additive is used together with the cinchonidium salt.

[10b] The method of the above-mentioned [10a], wherein the additive is sodium phenolate or sodium tert-butylalcoholate.

[11] The method of any of the above-mentioned [1] to [10], wherein the compound of the aforementioned formula [III] is produced by reacting a compound represented by the formula [IX]:

[IX]

or a salt thereof with a compound represented by the formula [X]:

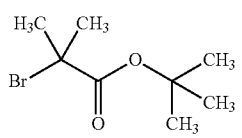

[X]

in the presence of a base.

[12] A method for producing a compound represented by the formula [I]:

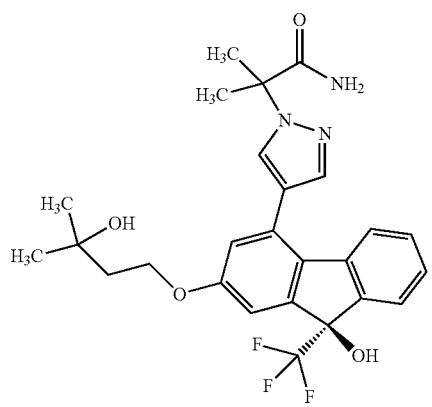

[I]

or a pharmaceutically acceptable salt thereof, or a hydrate thereof, wherein the method comprises a step of reacting a compound represented by the formula [VI]:

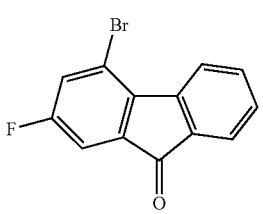

[VI]

with a compound represented by the formula [VII]:

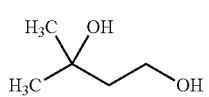

[VII]

in the presence of a base to convert same to a compound represented by the formula [VIII]:

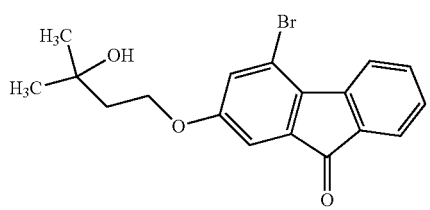
[VIII]

a step of reacting the compound of the formula [VIII] with (trifluoromethyl)trimethylsilane in the presence of an asymmetric organocatalyst and treating with an acid to give a compound represented by the formula [II]:

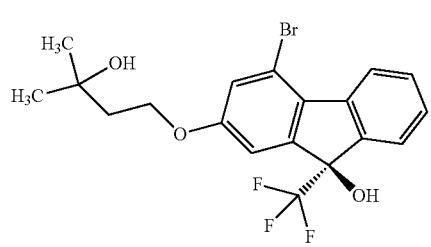
[II]

or a methanol solvate thereof, a step of reacting a compound represented by the formula [IX]:

[IX]

or a salt thereof with a compound represented by the formula [X]:

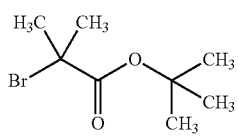
[X]

in the presence of a base to give a compound represented by the formula [III]:

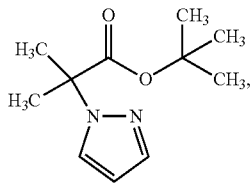
[III]

a step of subjecting the compound of the aforementioned formula [III] to a coupling reaction with the compound of the aforementioned formula [II] or a methanol solvate thereof in the presence of a metal catalyst, a base and carboxylic acid to convert the compound to a compound represented by the formula [IV]:

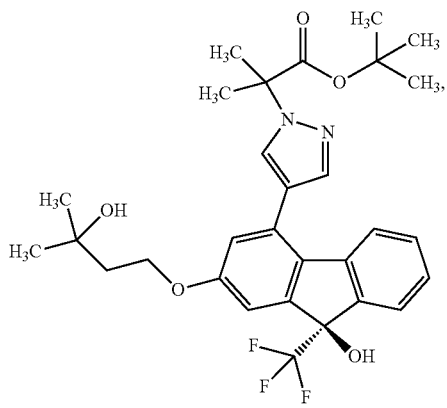
[IV]

a step of hydrolyzing the compound of the aforementioned formula [IV] to convert the compound to a compound represented by the formula [V]:

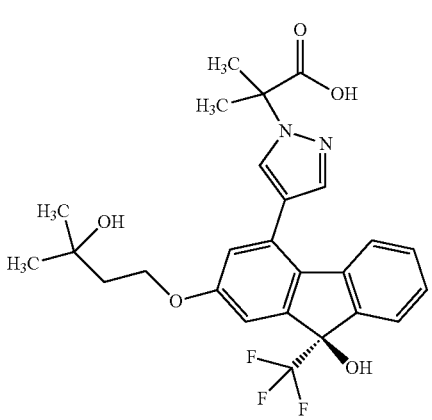
[V]

or a salt thereof, and a step of amidating the compound of the aforementioned formula [V] or a salt thereof by reacting with ammonia in the presence of a condensing agent.

[13] A method for producing a compound represented by the formula [IV]:

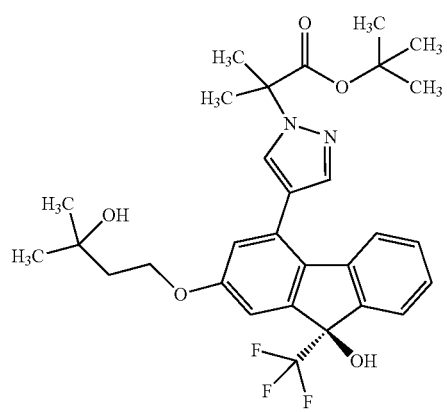
[IV]

comprising subjecting a compound represented by the formula [II]:

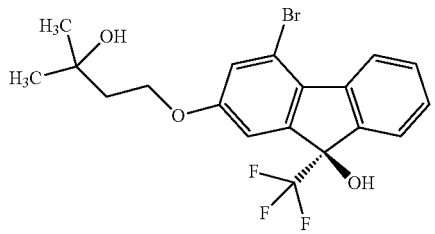

[II]

or a methanol solvate thereof to a coupling reaction with a compound represented by the formula [III]:

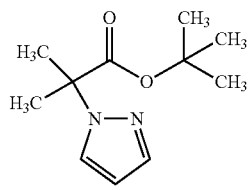

[III]

in the presence of a metal catalyst, a base and carboxylic acid.

[14] A compound or a pharmaceutically acceptable salt thereof produced by the method of any the above-mentioned [1] to [12].

[14a] A pharmaceutical composition comprising a compound or a pharmaceutically acceptable salt thereof produced by the method of the above-mentioned [1], and a pharmaceutically acceptable carrier.

[15] A compound represented by the formula [IV]:

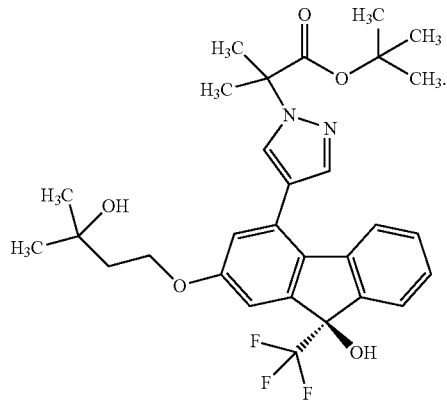

[IV]

[16] A compound represented by the formula [II]:

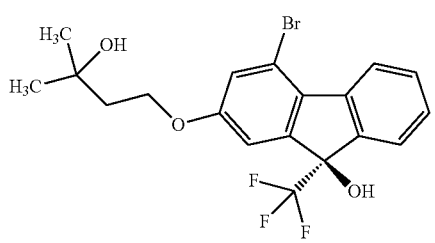

[II]

or a methanol solvate thereof.

[17] A compound represented by the formula [II]:

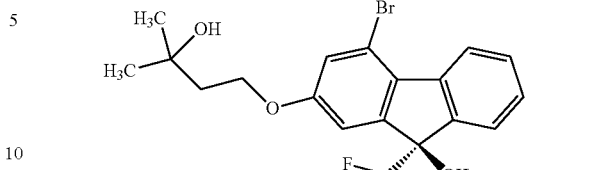

[II]

or the formula [IIm]:

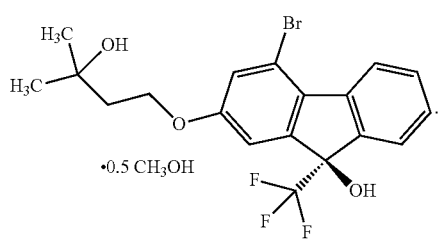

[IIm]

·0.5 CH$_3$OH

[18] A compound represented by the formula [III]:

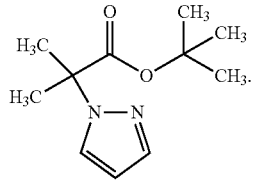

[III]

[18a] A compound represented by the formula [XV]:

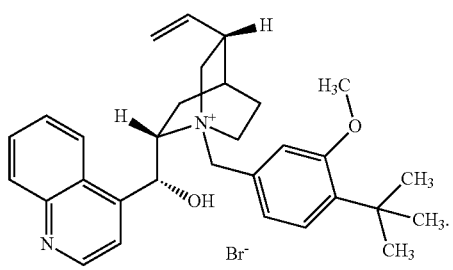

[XV]

According to the production method of the present invention, a pyrazole-amide compound having a PDHK inhibitory action and useful for the treatment or prophylaxis of diseases related to glucose metabolism disorder, diseases in which supply of energy substrate to tissues is restricted, mitochondrial disease, mitochondrial encephalomyopathy, cancer, pulmonary hypertension and the like can be produced in a high yield by a convenient operation via compounds easy to handle. By the present method, moreover, a novel intermediate for synthesizing the pyrazole-amide compound can be provided.

DESCRIPTION OF EMBODIMENTS

The definitions of the terms in the present specification are as follows.

The "metal catalyst" used for the coupling reaction only needs to be a transition metal catalyst usable for a coupling reaction (cross coupling reaction) and, for example, a palladium catalyst and the like can be mentioned. Among these, bis(triphenylphosphine)palladium(II) dichloride, [1,1'-bis (diphenylphosphino)ferrocene]palladium(II) dichloride dichloromethane adduct, palladium acetate and di(1-adamantyl)-n-butylphosphine, palladium acetate and dicyclohexyl(2,2-diphenyl-1-methylcyclopropyl)phosphine and the like are preferable.

The "base" used for the coupling reaction may be any base as long as it does not prevent progress of the coupling reaction and, for example, alkali metal carbonate, alkali metal acetate and the like can be mentioned. Among these, potassium carbonate is preferable.

The "carboxylic acid" used for the coupling reaction may be any carboxylic acid as long as it does not prevent progress of the coupling reaction and, for example, pivalic acid, isobutyric acid, propionic acid, benzoic acid and the like can be mentioned. Among these, pivalic acid or isobutyric acid is preferable, and pivalic acid is more preferable.

The "condensing agent" used for the reaction of the compound of the formula [V] or a salt thereof and ammonia may be any condensing agent as long as it is generally used for an amidation reaction of carboxylic acid and amine and, for example, 1-ethyl-3-(3-dimethylaminopropyl)carbodiimide hydrochloride, dicyclohexylcarbodiimide (DCC), 0-(benzotriazol-1-yl)-N,N,N',N'-tetramethyluronium tetrafluoroborate (TBTU), 2-(1H-7-azabenzotriazol-1-yl)-1,1, 3,3-tetramethyluronium hexafluorophosphate (HATU), 1,1'-carbonyldiimidazole and the like can be mentioned. Among these, 1-ethyl-3-(3-dimethylaminopropyl)carbodiimide hydrochloride which is a water-soluble condensing agent (WSC) is preferable. It is more preferable to use the condensing agent together with a conventional additive such as 1-hydroxybenzotriazole (HOBt) monohydrate, N-hydroxysuccinimide (HOSu), 6-chloro-1-hydroxybenzotriazole (Cl-HOBt), 1-hydroxy-7-aza benzotriazole (HOAt), 3-hydroxy-4-oxo-3,4-dihydro-1,2,3-benzotriazine and the like (preferably, 1-hydroxybenzotriazole monohydrate).

As "ammonia", (1) aqueous ammonia or (2) ammonia generated by ammonium chloride and trialkyl amine (e.g., triethylamine, diisopropylethylamine etc.) can be used.

The "asymmetric organocatalyst" means an organic compound to be the catalyst of an asymmetric reaction. Examples of the asymmetric organocatalyst usable for the conversion reaction of the compound of the formula [VIII] to the compound of the formula [II] include cinchonidium salt and the like, preferably, N-(4-tert-butyl-3-methoxybenzyl)cinchonidium bromide.

The "pharmaceutically acceptable salt" of the compound may be any salt as long as it forms a salt unaccompanied by excessive toxicity known in the pertinent art with the compound of the formula [I]. Examples thereof include salts with inorganic acids, salts with organic acids, salts with amino acids and the like.

Various forms of pharmaceutically acceptable salts are well known in the pertinent field and, for example, they are described in the following reference documents:

(a) Berge et al., J. Pharm. Sci., 66, p 1-19 (1977), (b) Stahl et al., "Handbook of Pharmaceutical Salts: Properties, Selection, and Use" (Wiley-VCH, Weinheim, Germany, 2002), (c) Paulekuhn et al., J. Med. Chem., 50, p 6665-6672 (2007).

Each of them can be obtained by reacting a compound of the formula [I] with an inorganic acid, organic acid or amino acid according to a method known per se.

Examples of the salt with inorganic acid include a salt with hydrochloric acid, nitric acid, sulfuric acid, phosphoric acid, hydrobromic acid and the like.

Examples of the salt with organic acid include salts with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salt with amino acid include salts with aspartic acid, glutamic acid and the like.

A pharmaceutically acceptable salt of the compound of the present invention is preferably a salt with an inorganic acid.

The "salt" of the compound may be any salt as long as it forms a salt with the compound of the present invention. Examples thereof include salts with inorganic acids, salts with organic acids, salts with inorganic bases, salts with organic bases, salts with amino acids and the like. For example, the aforementioned "pharmaceutically acceptable salt" can be mentioned.

Examples of the salt with inorganic base include salts with ammonium, aluminum, barium, bismuth, calcium, lithium, magnesium, potassium, sodium, zinc and the like.

Examples of the salt with organic base include salts with arecoline, clemizole, ethylenediamine, N-methylglucamine, N-benzylphenethylamine, tris(hydroxymethyl)methylamine and the like.

Examples of the salt with amino acid include salts with arginine, lysine and the like.

Each of them can be obtained by reacting the compound of the present invention and an inorganic base, organic base, inorganic acid, organic acid or amino acid according to a method known per se.

The compound of the present invention, a salt thereof, or a pharmaceutically acceptable salt thereof may exist as a solvate. The term "solvate" refers to the compound of the present invention, a salt thereof, or a pharmaceutically acceptable salt thereof with which a solvent molecule is coordinated, and also includes hydrates. Such solvates are preferably pharmaceutically acceptable solvates. Such solvates include, for example, hydrate, methanol solvate, ethanol solvate, dimethylsulfoxide-solvate and the like of the compound of the present invention, a salt thereof, or a pharmaceutically acceptable salt thereof. The "methanol solvate" refers to the compound of the present invention with which a methanol molecule is coordinated. For example, hemimethanol solvate and the like can be mentioned.

Examples of the "compound represented by the formula [I]:

[I]

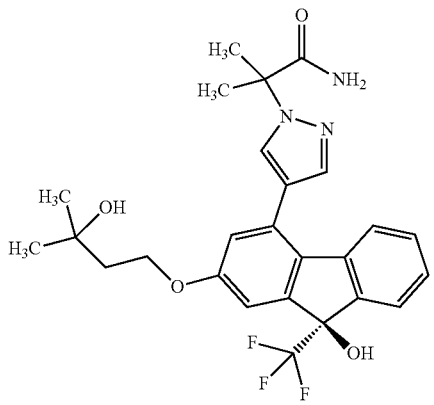

or a pharmaceutically acceptable salt thereof, or a hydrate thereof" include the following compounds compound (1)

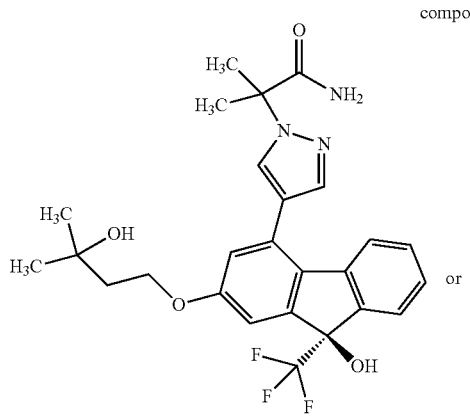

or compound (1h)

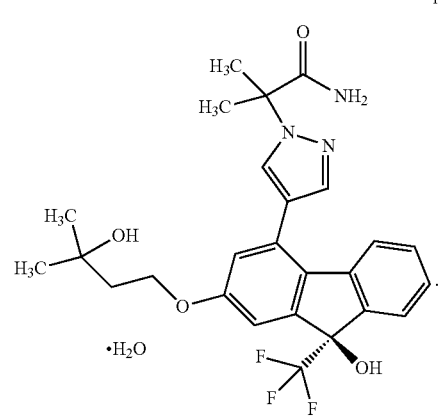

·H₂O

Examples of the "the compound represented by the formula [II]:

[II]

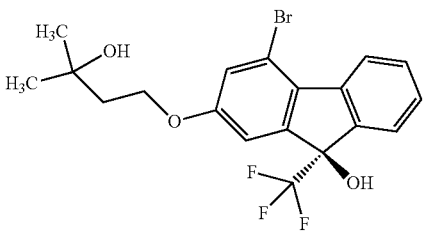

or a methanol solvate thereof" include the following compounds

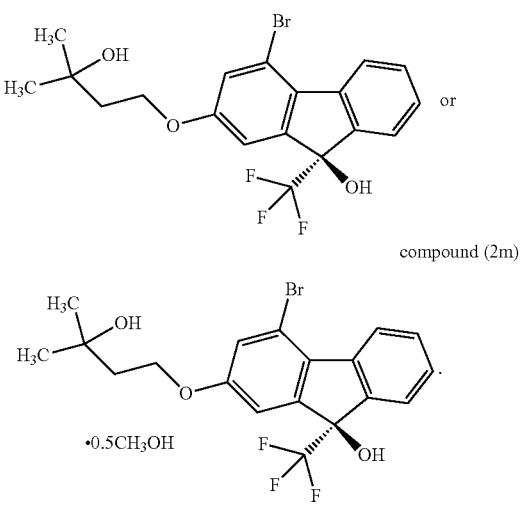

compound (2)

or compound (2m)

·0.5CH₃OH

The compound of the formula [I] or a pharmaceutically acceptable salt thereof, or a hydrate thereof may be labeled with an isotope element ($^2H$, $^3H$, $^{14}C$, $^{13}C$, $^{35}S$ etc.).

The compound of the formula [I] or a pharmaceutically acceptable salt thereof, or a hydrate thereof is preferably a substantially purified compound of the formula [I] or a hydrate thereof. Preferably, it is a compound of the formula [I] or a hydrate thereof that is purified to a purity of not less than 80%.

More preferably, it is a compound of the formula [I] or a hydrate thereof that is purified to a purity of not less than 90%.

The compound of the present invention or a pharmaceutically acceptable salt thereof, or a hydrate thereof may be a crystal, a non-crystal (amorphous), or a mixture thereof.

The pharmaceutical composition of the present invention may be produced according to a method known in the art of pharmaceutical preparations, by mixing the compound of the formula [I] or a pharmaceutically acceptable salt thereof, or a hydrate salt thereof with a suitable amount of at least one kind of pharmaceutically acceptable carrier and the like as appropriate.

While the content of the compound of the formula [I] or a pharmaceutically acceptable salt thereof, or a hydrate salt thereof varies depending on the dosage form, dose and the like, it is, for example, 0.1 to 100 wt % of the whole composition.

Examples of the dosage form of the compound of the formula [I] or a pharmaceutically acceptable salt thereof, or a hydrate thereof include oral preparations such as tablet, capsule, granule, powder, troche, syrup, emulsion, suspension and the like, or parenteral agents such as external preparation, suppository, injection, eye drop, nasal preparation, pulmonary preparation and the like.

The "reaction temperature" means temperature in a reaction solution, the "inside temperature" means temperature in a reaction mixture, a suspension and the like, and the "outer temperature" means temperature in an oil bath, a water bath or a drying oven.

It is defined that "about" means ±5° C. for temperature, ±10 min for time, and ±10% for weight and volume.

The main steps of the production method of the present invention are specifically explained in the following.

In each step, a reaction workup may be performed according to a method generally employed. The resultant product may be purified by appropriately selecting a conventional method such as distillation, crystallization, recrystallization, column chromatography, preparative HPLC, slurry wash and the like, or using them in combination. It is also possible to proceed to a next step without performing isolation or purification.

Step 4

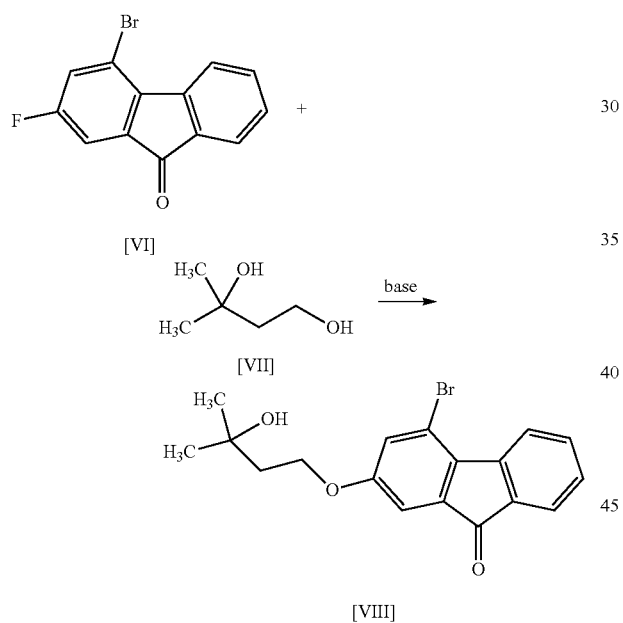

The compound of the formula [VIII] is obtained by reacting the compound of the formula [VI] with the compound of the formula [VII].

This reaction is performed in a solvent that does not adversely influence the reaction and in the presence of a base.

Examples of the solvent include hydrocarbons such as hexane, toluene and the like, ethers such as 1,4-dioxane, tetrahydrofuran, 1,2-dimethoxyethane and the like, sulfoxides such as dimethyl sulfoxide and the like, amides such as N,N-dimethylacetamide, N-methyl-2-pyrrolidone and the like, water, and a mixture thereof. Among these, toluene/water/tetrahydrofuran is preferable.

Examples of the base include tripotassium phosphate, cesium carbonate, potassium tert-butoxide, sodium hydroxide and the like, preferably sodium hydroxide.

The amount of the base to be used is 2 to 20 mol, preferably 10 to 20 mol, more preferably 19 to 20 mol, per 1 mol of the compound of the formula [VI].

This reaction is preferably performed in the presence of a phase-transfer catalyst.

Examples of the phase-transfer catalyst include tetra n-butylammonium hydroxide, tetra n-butylammonium hydrogen sulfate, tetra n-butylammonium fluoride and the like. Among these, tetra n-butylammonium hydroxide is preferable. The amount of the phase-transfer catalyst to be used is 0.1 to 1.5 mol, preferably 0.4 to 0.8 mol, more preferably 0.6 to 0.8 mol, per 1 mol of the compound of the formula [VI].

The amount of the compound of the formula [VII] to be used is 1 to 4 mol, preferably 2 to 3 mol, per 1 mol of the compound of the formula [VI].

The reaction temperature and the reaction time are respectively about 15° C. to about 50° C. and about 1 hr to about 24 hr. A preferable reaction temperature is room temperature and a preferable reaction time is about 4 hr to about 10 hr.

Step 5

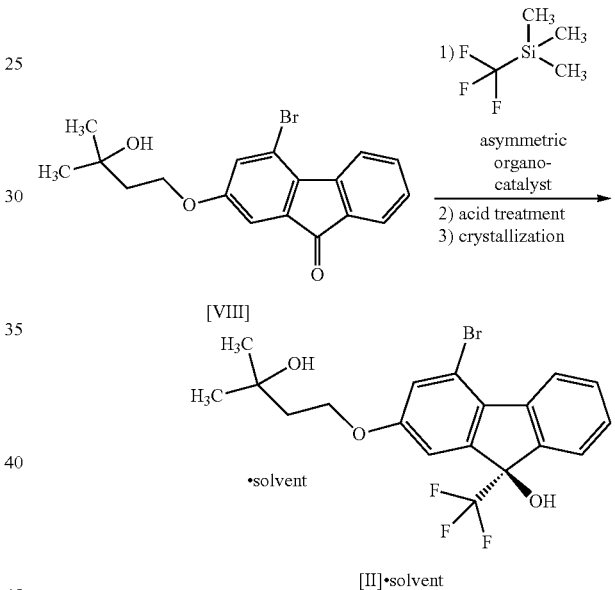

This step includes operation 1 for reacting the compound of the formula [VIII] with (trifluoromethyl)trimethylsilane in the presence of an asymmetric organocatalyst, operation 2 for treating a trimethylsilyl form of the compound represented by the formula [II] obtained in operation 1 with an acid to remove the trimethylsilyl group, and operation 3 for obtaining crystals of the solvate of the compound of formula [II] by crystallizing the compound obtained in operation 2.

The detail of the operations 1 to 3 is explained below.

Operation 1

Operation 1 is performed in a solvent that does not adversely influence the reaction and in the presence of an asymmetric organocatalyst. The asymmetric organocatalyst is not particularly limited and, for example, cinchonidium salt can be mentioned. Examples of the cinchonidium salt include N-(4-tert-butyl-3-methoxybenzyl)cinchonidium fluoride, N-(4-tert-butyl-3-methoxybenzyl)cinchonidium bromide, N-(4-tert-butyl-3-methoxybenzyl)cinchonidium p-methoxyphenoxide and the like. Among these, N-(4-tert-butyl-3-methoxybenzyl)cinchonidium bromide is preferable as the cinchonidium salt.

The amount of the asymmetric organocatalyst to be used is 0.005 to 0.3 mol, preferably 0.01 to 0.1 mol, particularly preferably 0.05 mol, per 1 mol of the compound of the formula [VIII].

An asymmetric organocatalyst is used together with an additive where necessary. Examples of the additive include sodium phenolate, sodium tert-butylalcoholate and the like. Among these, equimolar amount of sodium phenolate is preferable as the additive.

Examples of the solvent include aromatic hydrocarbons such as toluene, xylene and the like, ethers such as tetrahydrofuran, diethyl ether, 1,4-dioxane, 1,2-dimethoxyethane and the like, and the like. Among these, a mixed solvent of toluene and tetrahydrofuran is preferable.

The reaction temperature is about −78° C. to about 0° C., preferably about −55° C. to about −45° C.

The reaction time is about 2 hr to about 8 hr, preferably about 5 hr.

Operation 2

Operation 2 is performed in a solvent that does not adversely influence the reaction and in the presence of an acid, and a solution containing the compound of the formula [II] is obtained.

Examples of the solvent include alcohols such as methanol, ethanol, 2-propanol and the like. Among these, methanol is preferable.

While the acid is not particularly limited, for example, trifluoroacetic acid, hydrochloric acid and the like can be mentioned, with preference given to hydrochloric acid.

The amount of the acid to be used is 0.2 to 5.0 mol, preferably 0.3 to 2.0 mol, per 1 mol of the compound of the formula [VIII].

The reaction temperature is preferably room temperature.

The reaction time is about 1 hr to about 6 hr, preferably about 3 hr.

Operation 3

The crystallization in operation 3 is performed in a water-containing solvent, and the compound of the formula [II] is obtained as a solvate (alcohol solvate (preferably, methanol solvate)).

Examples of the solvent include alcohols such as methanol, ethanol, 2-propanol and the like. Preferred is methanol.

The "methanol solvate of the compound of the formula [II]" may be a mixture of the compound of the formula [II] and a methanol solvate of the compound of the formula [II] depending on the drying conditions and the like.

Step 6

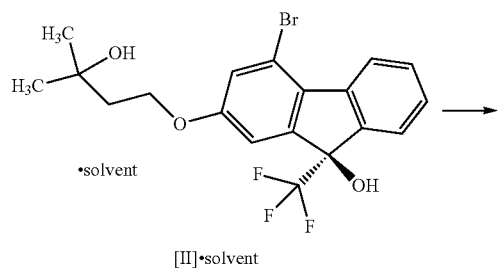

[II]·solvent

-continued

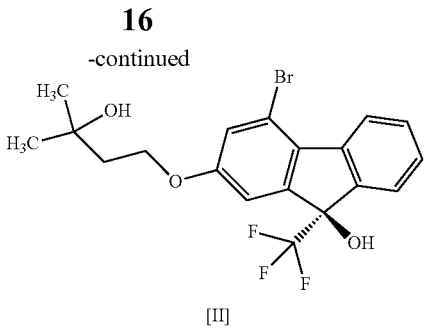

[II]

In Step 6, a solvent is added to the solvate of the compound of the formula [II] obtained in the aforementioned Step 5, the resulting suspension is stirred with heating, the solvent is evaporated under reduced pressure, the residue is resuspended in the solvent, and the suspension is stirred, filtered, washed and dried to give the compound of the formula [II] as a crystal.

Examples of the solvent used for preparing the suspension of the solvate of the compound of the formula [II] include aliphatic hydrocarbons such as hexane, heptane, octane and the like and/or aromatic hydrocarbons such as benzene, toluene, xylene and the like. Among these, heptane is preferable.

The stirring temperature is an inside temperature of about 60° C. to the boiling point of the solvent, preferably an inside temperature of not less than 85° C.

The stirring time is about 1 hr to about 6 hr, preferably about 3 hr to about 5 hr.

Step 7

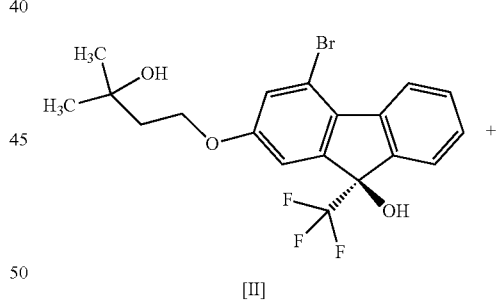

[II]

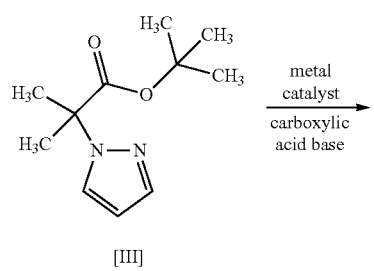

[III]

-continued

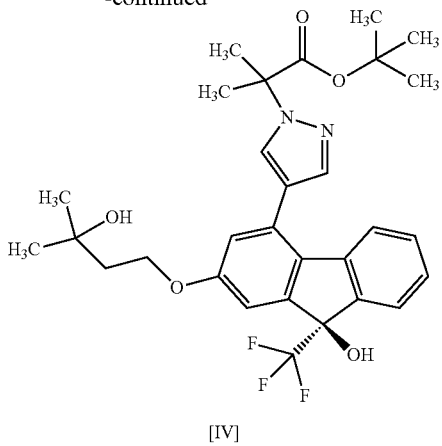

[IV]

The compound of the formula [IV] is obtained by subjecting the compound of the formula [II] or a methanol solvate thereof to a coupling reaction with the compound of the formula [III] in the presence of a metal catalyst. For the coupling reaction, the compound of the formula [II] is more preferable than the methanol solvate of the compound of the formula [II].

This reaction is performed in a solvent that does not adversely influence the reaction and in the presence of carboxylic acid and a base.

Examples of the solvent include ethers such as tetrahydrofuran, 1,4-dioxane and the like, nitriles such as acetonitrile and the like, amides such as N,N-dimethylformamide, N-methylpyrrolidone, N,N-dimethylacetamide and the like and hydrocarbons such as benzene, toluene and the like. Among these, N,N-dimethylacetamide is preferable.

Examples of the metal catalyst include palladium catalyst and the like. Among these, bis(triphenylphosphine)palladium(II) dichloride, [1,1'-bis(diphenylphosphino)ferrocene]palladium(II) dichloride dichloromethane adduct, palladium acetate and di(1-adamantyl)-n-butylphosphine, palladium acetate and dicyclohexyl(2,2-diphenyl-1-methylcyclopropyl)phosphine, and the like are preferable. Among these, bis(triphenylphosphine)palladium(II) dichloride is more preferable as the metal catalyst.

Examples of the carboxylic acid include pivalic acid, isobutyric acid, propionic acid, benzoic acid and the like. The carboxylic acid is preferably pivalic acid or isobutyric acid, more preferably pivalic acid.

Examples of the base include alkali metal carbonate, alkali metal acetate and the like, and preferred is potassium carbonate.

The amount of the compound of the formula [III] to be used is 1.0 to 5.0 mol, preferably 1.6 to 2.0 mol, per 1 mol of the compound of the formula [II].

The amount of the metal catalyst to be used is 0.005 to 0.2 mol, preferably 0.01 to 0.025 mol, per 1 mol of the compound of the formula [II].

The amount of the carboxylic acid to be used is 0.1 to 1.0 mol, preferably 0.2 to 0.5 mol, per 1 mol of the compound of the formula [II].

The amount of the base to be used is 0.4 to 4.0 mol, preferably 0.6 to 1.8 mol, per 1 mol of the compound of the formula [II].

The reaction temperature is about 80° C. to about 150° C., preferably about 90° C. to about 140° C., more preferably about 100° C. to about 110° C.

The reaction time is about 1 hr to about 6 hr, preferably about 3 hr.

Step 8

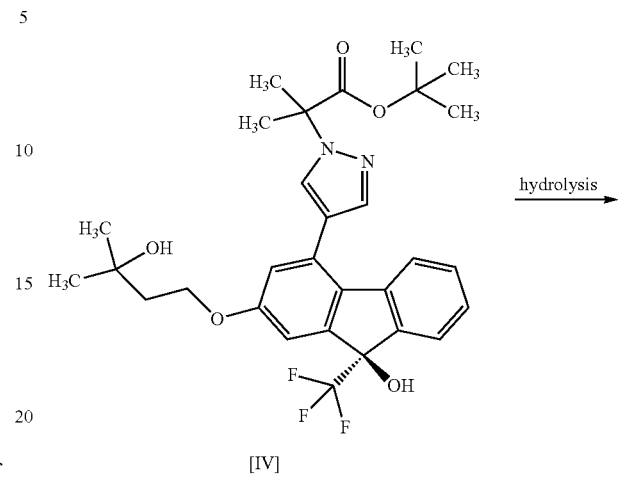

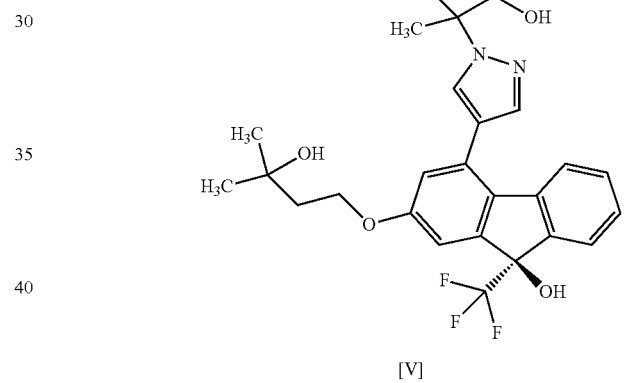

[V]

The compound of the formula [V] is obtained by hydrolyzing the compound of the formula [IV].

This reaction is performed in a solvent that does not adversely influence the reaction and in the presence of a base.

Examples of the solvent include alcohols such as methanol, ethanol, 2-propanol and the like, water and the like, and a mixture thereof. Among these, a mixed solvent of ethanol and water is preferable.

Examples of the base include inorganic bases such as sodium hydroxide, potassium hydroxide and the like. Among these, sodium hydroxide is preferable.

The amount of the base to be used is 7 to 16 mol, preferably 10 to 13 mol, per 1 mol of the compound of the formula [IV].

The reaction temperature is inside temperature of about 25° C. to the boiling point of the solvent, preferably about 70° C.

The reaction time is about 1 hr to about 8 hr, preferably about 1.5 hr.

Step 9

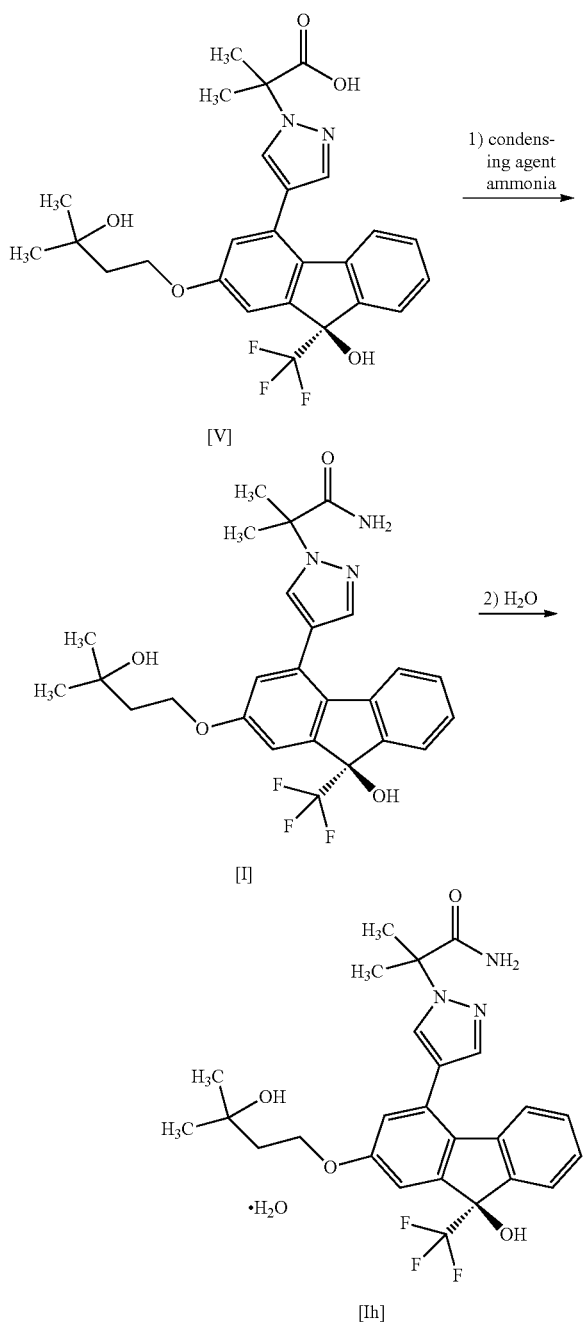

The compound of the formula [Ih] is obtained by performing operation 1 for reacting the compound of the formula [V] with ammonia in the presence of a condensing agent, after which operation 2 for crystallizing in a water-containing solvent.

Operation 1

The reaction of operation 1 is performed in a solvent that does not adversely influence the reaction and in the presence of a condensing agent.

Examples of the condensing agent include 1-ethyl-3-(3-dimethylaminopropyl)carbodiimide hydrochloride, dicyclohexylcarbodiimide (DCC), O-(benzotriazol-1-yl)-N,N,N',N'-tetramethyluronium tetrafluoroborate (TBTU), 2-(1H-7-azabenzotriazol-1-yl)-1,1,3,3-tetramethyluronium hexafluorophosphate (HATU), 1,1'-carbonyldiimidazole and the like. Among these, 1-ethyl-3-(3-dimethylaminopropyl) carbodiimide hydrochloride is preferable. These can be used singly or in combination with an additive (e.g., 1-hydroxybenzotriazole (HOBt) monohydrate, N-hydroxysuccinimide (HOSu), 6-chloro-1-hydroxybenzotriazole (Cl-HOBt), 1-hydroxy-7-azabenzotriazole (HOAt) or 3-hydroxy-4-oxo-3,4-dihydro-1,2,3-benzotriazine and the like, preferably 1-hydroxybenzotriazolemonohydrate). Among these, a combination of 1-ethyl-3-(3-dimethylaminopropyl)carbodiimide hydrochloride and 1-hydroxybenzotriazolemonohydrate is used particularly preferably.

The amount of the condensing agent to be used is 1 to 10 mol, preferably 1 to 2 mol, per 1 mol of the compound of the formula [V].

The amount of the additive to be used is 1 to 10 mol, preferably 1 to 2 mol, per 1 mol of the compound of the formula [V].

The amount of ammonia to be used when, for example, aqueous ammonia is used is 1 to 3 mol, preferably 1 to 2 mol, based on the amount of ammonia, per 1 mol of the compound of the formula [V].

In addition, ammonium chloride and a base (e.g., trialkyl amine, specifically, triethylamine, diisopropylethylamine etc.) can be used as ammonia.

Examples of the solvent include ethers such as diethyl ether, 1,4-dioxane, tetrahydrofuran and the like, esters such as ethyl acetate and the like, halogenated hydrocarbons such as chloroform, dichloromethane and the like, amides such as N,N-dimethylformamide and the like, a mixture thereof and the like, and they may be mixed as appropriate. Among these, N,N-dimethylformamide is preferable.

The reaction temperature varies depending on the kind of the solvent and is about 0° C. to about 40° C., preferably about 15° C. to about 30° C. The reaction time is about 0.5 hr to about 24 hr, preferably about 1.5 hr to about 8 hr.

Operation 2

In operation 2, alcohol (e.g., ethanol) is added as a solvent to a solution of the compound of the formula [I] obtained in the aforementioned operation 1, and an azeotropic distillation operation for evaporating a part of the solvent under reduced pressure is repeated. Alcohol is further added to give a solution, the inside temperature thereof is raised to about 40° C. to about 50° C., water is added dropwise at the same temperature, after stirring, the inside temperature of the resulting suspension is raised to about 55° C. to about 65° C., the suspension is stirred and allowed to gradually return to room temperature, and the obtained mixture is further stirred, whereby the compound of the formula [Ih] can be precipitated as crystals.

The stirring time is about 1 hr to about 7 hr, preferably about 2 hr, at an inside temperature of about 40° C. to about 50° C., about 1 hr to about 4 hr, preferably about 1 hr to about 2 hr, at an inside temperature of about 55° C. to about 65° C., and about 8 hr to 24 hr, preferably about 12 hr, at room temperature.

In operation 2, the crystallization operation may be performed by adding a seed crystal of the compound of the formula [Ih] after dropwise addition of water.

Step 10

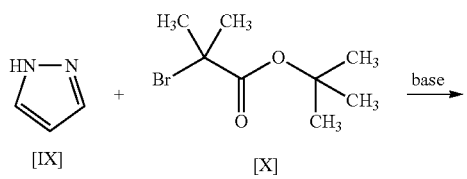

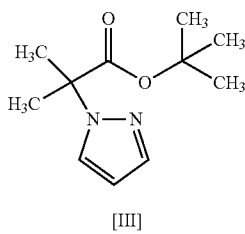

The compound of the formula [III] is obtained by reacting the compound of the formula [IX] with the compound of the formula [X].

This reaction is performed in a solvent that does not adversely influence the reaction and in the presence of a base.

Examples of the solvent include ethers such as tetrahydrofuran, 1,4-dioxane, 1,2-dimethoxyethane and the like, hydrocarbons such as hexane, toluene and the like, amides such as N,N-dimethylformamide, N,N-dimethylacetamide and the like, and a mixture thereof. Among these, tetrahydrofuran is preferable.

Examples of the base include sodium hydride, potassium tert-butoxide, sodium methoxide, sodium bis (trimethylsilyl) amide, cesium carbonate and the like, with preference given to sodium hydride.

The amount of the base to be used is 1 to 2 mol, preferably 1 to 1.5 mol, per 1 mol of the compound of the formula [IX].

The amount of the compound of the formula [X] to be used is 1 to 1.5 mol, preferably 1 to 1.2 mol, per 1 mol of the compound of the formula [IX].

The reaction temperature is room temperature to the boiling point of the solvent, preferably about 50° C. to about 65° C.

The reaction time is from about 1 hr to about 24 hr.

As characteristics of the production method, the following can be mentioned.

1. Compound (2) or Compound (2m)

1-1.

Compound (2) could be purified to give a compound having good chemical purity and good optical purity (e.g., 95% e.e. or more) by a single operation by converting to a methanol solvate (compound (2m)) having good crystallinity.

2. Compound (3)

2-1.

Compound (3) could be purified to achieve a purity of not less than 90% by distillation (not less than 99% depending on distillation conditions).

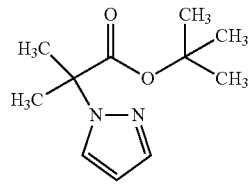

compound (3)

3. Coupling Reaction 3-1.

When compound (2) and compound (3) were used under particular coupling reaction conditions, the side reaction of the coupling reaction could be suppressed more than when compound (2) and compound (101) mentioned below were used.

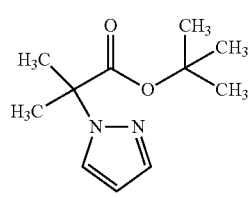

compound (3)

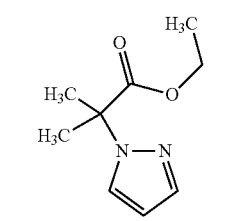

compound (101)

3-2.

When compound (3) and compound (2) were used under particular coupling reaction conditions, the object coupling product could be obtained in a higher yield than when compound (3) and compound (102) (chloro compound (racemate) mentioned below) were used.

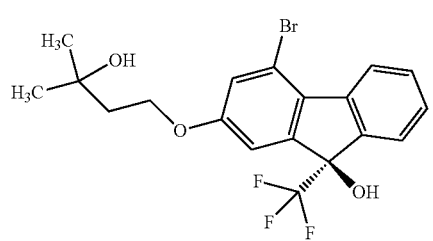

compound (2)

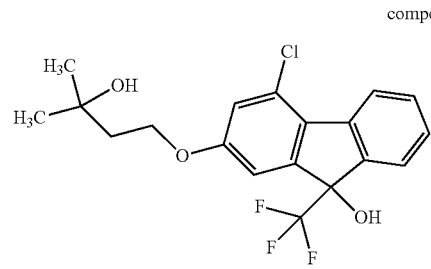

compound (102)

EXAMPLES

While the present invention is explained in detail by referring to the following Examples, the present invention is not limited thereto.

Even if no description is found in the production methods in the following Examples, steps may be modified for efficient production, such as introduction of a protecting group into a functional group where necessary with deprotection in a subsequent step, using a functional group as a precursor in each step, followed by conversion to a desired functional group at a suitable stage, changing the order of production methods and steps, and the like.

The reaction workup in each step may be performed by a conventional method, where isolation and purification can be performed as necessary according to a method appropriately selected from conventional methods such as crystallization, recrystallization, distillation, partitioning, silica gel chromatography, preparative HPLC and the like, or a combination thereof. All reagents and solvents have quality of commercially available products, and were used without purification.

Note that % indicates mol/mol % for yield, and wt % for others unless particularly indicated. In addition, room temperature indicates a temperature of 15 to 30° C. unless particularly indicated. Other abbreviations used in the example section mean the following.

s: singlet
d: doublet
t: triplet
q: quartet
m: multiplet
br: broad
dd: double doublet
ddd: double double doublet
dddd: double double double doublet
J: coupling constant
MeOH: methanol
DMSO-$D_6$: deuterodimethyl sulfoxide
$^1$H-NMR: proton nuclear magnetic resonance
HPLC: high performance liquid chromatography $^1$H-NMR spectrum was measured in DMSO-$D_6$ using tetramethylsilane as an internal standard, and all δ values are shown in ppm.

(Phosphate buffer (pH 2.0))

Sodium dihydrogen phosphate dihydrate (4.68 g) was dissolved in water (3000 ml), and phosphoric acid (5 mL) was added to give the title buffer.

HPLC Analysis Conditions

In the following analysis conditions, "%" indicates % by volume. The gradient linearly changes the mixing ratio of SOLUTION A and SOLUTION B.

Analysis Condition 1
Measurement device: HPLC system Waters Alliance
  Column: Waters SunFire C18 3.5 µm 4.6 mmφ×150 mm
  Column temperature: 40° C.
Mobile phase: (SOLUTION A) phosphate buffer (pH2.0), (SOLUTION B) acetonitrile

| Gradient profile: | time (min) | 0 | 30 | 35 | 40 | 45 | (stop) |
|---|---|---|---|---|---|---|---|
| | A (%) | 70 | 25 | 25 | 70 | 70 | |
| | B (%) | 30 | 75 | 75 | 30 | 30 | |

Analysis time: 45 min
Flow rate: 1.0 mL/min
Detection: UV (220 nm)
Analysis Condition 2
Measurement device: HPLC system Waters Alliance
  Column: Waters SunFire C8 3.5 µm 4.6 mmφ×150 mm
  Column temperature: 40° C.
Mobile phase: (SOLUTION A) distilled water, (SOLUTION B) acetonitrile

| Gradient profile: | time (min) | 0 | 20 | 35 | 36 | 40 | (stop) |
|---|---|---|---|---|---|---|---|
| | A (%) | 60 | 10 | 10 | 60 | 60 | |
| | B (%) | 40 | 90 | 90 | 40 | 40 | |

Analysis time: 40 min
Flow rate: 1.0 mL/min
Detection: UV (220 nm)
Analysis Condition 3
Measurement device: HPLC system Waters Alliance
  Column: Daicel Corporation CHIRALCEL OD-3R 3 µm 4.6 mmφ×150 mm
  Column temperature: 40° C.
Mobile phase: (SOLUTION A) phosphate buffer (pH 2.0), (SOLUTION B) acetonitrile

| Gradient profile: | time (min) | 0 | 20 | 30 | 40 | 45 | (stop) |
|---|---|---|---|---|---|---|---|
| | A (%) | 70 | 40 | 40 | 70 | 70 | |
| | B (%) | 30 | 60 | 60 | 30 | 30 | |

Analysis time: 45 min
Flow rate: 0.5 mL/min
Detection: UV (254 nm)
Analysis Condition 4
Measurement device: HPLC system Waters Alliance
  Column: Daicel Corporation CHIRALCEL OJ-3R 3 µm 4.6 mmφ×150 mm
  Column temperature: 40° C.
Mobile phase: (SOLUTION A) phosphate buffer (pH 2.0), (SOLUTION B) acetonitrile
Composition of mobile phase: SOLUTION A:SOLUTION B=70:30
Analysis time: 15 min
Flow rate: 1.0 mL/min
Detection: UV (220 nm)

Example 1

Synthesis of 2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropanamide monohydrate (Compound (1h))

Step 1

(2-Amino-3-bromo-5-fluorophenyl)(phenyl)methanone (Compound (12))

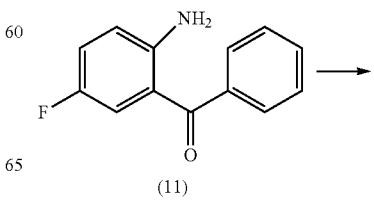

(11)

-continued

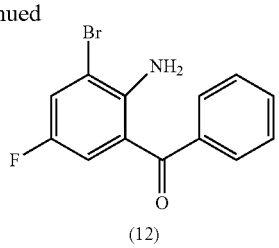

To a suspension of (2-amino-5-fluorophenyl)(phenyl)methanone (compound (11)) (50.0 g) in acetic acid (400 mL) was added dropwise at an inside temperature of 21 to 30° C. about 65% of the whole weight of a bromine (40.8 g)/acetic acid (90 mL) solution. After completion of the dropwise addition, a seed crystal (5 mg) of (2-amino-3-bromo-5-fluorophenyl)(phenyl)methanone (compound (12)) hydrobromide was added and crystal precipitation was visually confirmed. The obtained suspension was heated to an inside temperature of 41° C., and the total amount (about 35%) of the rest of the bromine (40.8 g)/acetic acid (90 mL) solution was added dropwise at an inside temperature of 41 to 45° C. The dropping funnel was washed with acetic acid (10 mL), and the mixture was stirred at an inside temperature of 45 to 46° C. for 17 min. To the obtained suspension was added dropwise a sodium sulfite (4.39 g)/water (45 mL) solution at an inside temperature of 41 to 45° C., the dropping funnel was washed with water (5 mL), and the mixture was stirred at an inside temperature of 41 to 46° C. for 30 min. To the obtained suspension was added dropwise water (50 mL) at an inside temperature of 43 to 46° C., a seed crystal (5 mg) of (2-amino-3-bromo-5-fluorophenyl)(phenyl)methanone (compound (12)) was added and the mixture was stirred for 5 min. After crystal precipitation was visually confirmed, water (350 mL) was added dropwise at an inside temperature of 47 to 51° C., and the mixture was stirred at an inside temperature of 50 to 55° C. for 1 hr. The obtained suspension was cooled to room temperature and stirred overnight. The precipitated solid was collected by filtration, and washed with water (100 mL) and dried under reduced pressure to give the title compound (65.2 g).
$^1$H-NMR (400 MHz, DMSO-D$_6$) δ: 7.78 (dd, 1H, J=7.8, 3.0 Hz), 7.67-7.61 (m, 3H), 7.58-7.51 (m, 2H), 7.11 (dd, 1H, J=9.3, 3.0 Hz), 6.73 (brs, 2H).

Synthesis of seed crystal of (2-amino-3-bromo-5-fluorophenyl)(phenyl)methanone (Compound (12)) hydrobromide Used in Step 1

To a solution of (2-amino-3-bromo-5-fluorophenyl)(phenyl)methanone (compound (12)) (1.00 g) in toluene (25 mL) was added an acetic acid solution (0.87 mL) of 25% hydrobromic acid at room temperature. The precipitated solid was collected by filtration and washed with toluene. The obtained solid was dried under reduced pressure to give a seed crystal (1.21 g) of (2-amino-3-bromo-5-fluorophenyl)(phenyl)methanone (compound (12)) hydrobromide.

Synthesis of Seed Crystal of (2-amino-3-bromo-5-fluorophenyl)(phenyl)methanone (Compound (12)) Used in Step 1:

The seed crystal of the title compound (2-amino-3-bromo-5-fluorophenyl)(phenyl)methanone (compound (12)) was obtained by the same method as in the aforementioned Step 1 except that a seed crystal was not added.

Step 2

4-Bromo-2-fluoro-9H-fluoren-9-one (Compound (6))

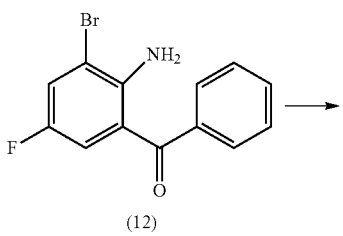
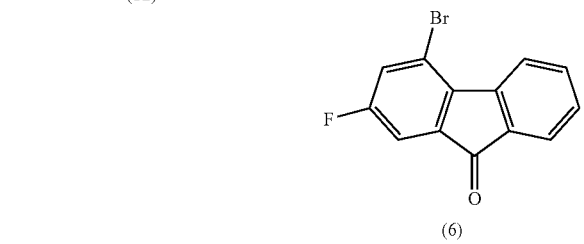

Under a nitrogen atmosphere, (2-amino-3-bromo-5-fluorophenyl)(phenyl)methanone (compound (12)) (25.0 g), cuprous oxide (7.30 g) and acetic acid (150 mL) were added, and 64% sulfuric acid (150 mL) was added with stirring the mixture at room temperature. The obtained suspension was heated to an inside temperature of 65° C., a sodium nitrite (8.80 g)/water (87.5 mL) solution was added dropwise at an inside temperature of 66 to 68° C., the dropping funnel was washed with water (13 mL) and the mixture was stirred at an inside temperature of 65 to 70° C. for 30 min. The obtained reaction mixture was cooled to room temperature, a sodium sulfite (8.57 g)/water (62.5 mL) solution was added dropwise at an inside temperature of 23 to 24° C., the dropping funnel was washed with water (13 mL) and the mixture was stirred at room temperature for 30 min. To the obtained mixture was added toluene (375 mL) and the mixture was stirred for 30 min. Insoluble material was filtered off through celite and washed with toluene (75 mL). The obtained filtrate and washing were partitioned, the aqueous layer was removed, and the organic layer was washed successively with water (125 mL×2 times), 5% aqueous sodium hydrogen carbonate solution (125 mL) and 1% brine (125 mL). The obtained organic layer was concentrated under reduced pressure and the toluene (about 375 mL) was evaporated. To the residue was added 2-propanol (250 mL) and the mixture was concentrated under reduced pressure until the weight became about 90 g. A similar operation was performed two more times, 2-propanol (150 mL) was added and the weight was adjusted to 207 g. The obtained suspension was heated under reflux for 30 min, successively stirred at an outer temperature of 75° C. for 1 hr and an outer temperature of 60° C. for 1 hr, cooled to room temperature and stirring was stopped. After standing at room temperature overnight, the precipitated solid was collected by filtration and washed with 2-propanol (50 mL). The obtained solid was dried under reduced pressure to give the title compound (15.6 g).

$^1$H-NMR (400 MHz, DMSO-D$_6$) δ: 8.27 (dd, 1H, J=8.2, 0.9 Hz), 7.79 (dd, 1H, J=8.8, 2.3 Hz), 7.72-7.67 (m, 2H), 7.51 (dd, 1H, J=6.8, 2.3 Hz), 7.46 (ddd, 1H, J=7.6, 7.6, 0.9 Hz).

Step 3

Synthesis of N-(4-tert-butyl-3-methoxybenzyl)cinchonidium bromide (Compound (15))

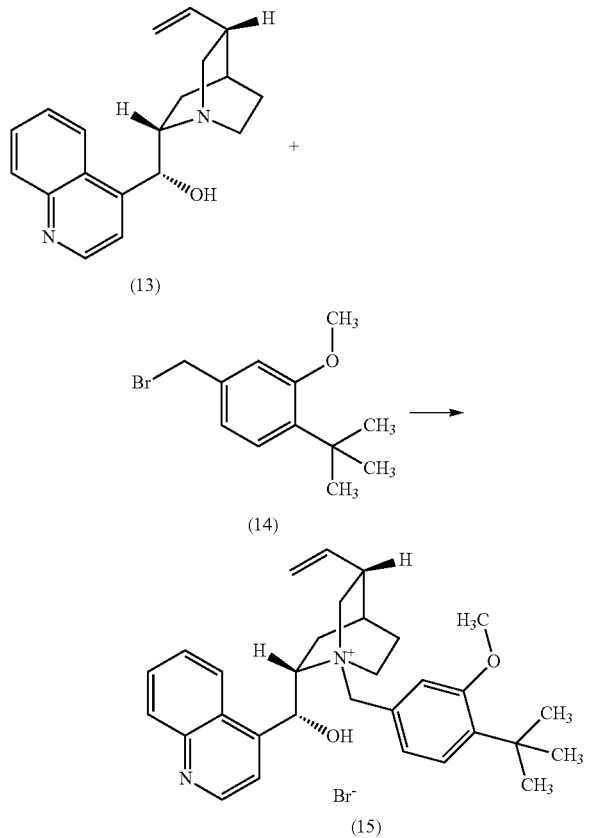

Under a nitrogen atmosphere, cinchonidine (compound (13)) (2.50 g), tetrahydrofuran (43 mL) and 4-tert-butyl-3-methoxybenzyl bromide (compound (14)) (2.29 g) were added, and the obtained mixture was stirred at 61 to 62° C. for 7 hr. The reaction mixture was cooled to room temperature, and solid was collected by filtration and washed with tetrahydrofuran (10 mL). The obtained solid was dried under reduced pressure to give the title compound (4.41 g).

$^1$H-NMR (400 MHz, DMSO-D$_6$) δ: 8.99 (d, 1H, J=4.4 Hz), 8.29 (d, 1H, J=8.3 Hz), 8.11 (dd, 1H, J=8.6, 1.4 Hz), 7.88-7.82 (m, 1H), 7.81 (d, 1H, J=4.4 Hz), 7.78-7.72 (m, 1H), 7.39 (d, 1H, J=8.1 Hz), 7.34 (d, 1H, J=1.8 Hz), 7.22 (dd, 1H, J=8.1, 1.8 Hz), 6.72 (d, 1H, J=4.6 Hz), 6.55 (d, 1H, J=4.6 Hz), 5.69 (ddd, 1H, J=17.4, 10.6, 6.5 Hz), 5.16 (dd, 1H, J=17.4, 1.4 Hz), 5.10 (d, 1H, J=12.2 Hz), 4.97 (d, 1H, J=12.2 Hz), 4.96 (dd, 1H, J=10.6, 1.4 Hz), 4.36-4.23 (m, 1H), 3.96-3.84 (m, 1H), 3.89 (s, 3H), 3.80-3.69 (m, 1H), 3.40-3.25 (m, 2H), 2.77-2.65 (m, 1H), 2.20-1.96 (m, 3H), 1.91-1.79 (m, 1H), 1.38 (s, 9H), 1.38-1.26 (m, 1H).

Step 4

4-Bromo-2-(3-hydroxy-3-methylbutyloxy)-9H-fluoren-9-one (Compound (8))

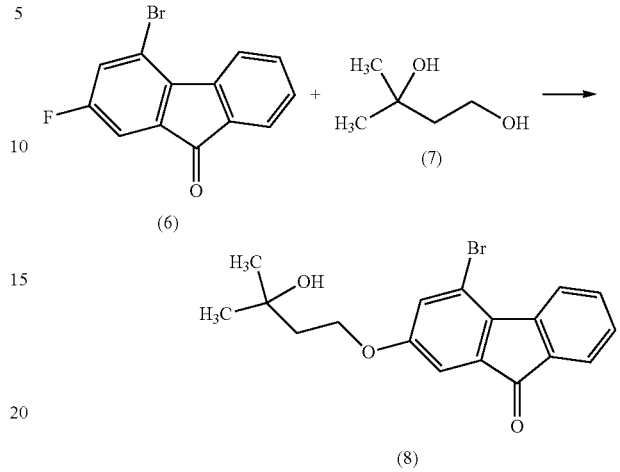

Under a nitrogen atmosphere, to 4-bromo-2-fluoro-9H-fluoren-9-one (compound (6)) (25.0 g) were added 3-methyl-1,3-butanediol (18.8 g) (compound (7)), toluene (188 mL) and tetrahydrofuran (25 mL), and the mixture was cooled in an ice bath. To the obtained mixture were added dropwise 55% aqueous tetra n-butylammonium hydroxide solution (27.5 mL), 40% aqueous sodium hydroxide solution (100 mL) and water (10 mL) at an inside temperature of 3.6 to 7.9° C., and the mixture was stirred at room temperature for 9 hr 30 min. To the obtained reaction mixture was added dropwise water (125 mL) at an inside temperature of 18 to 24° C., and the mixture was extracted with toluene (188 mL). The aqueous layer was removed. The organic layer was washed successively with water (125 mL), 5% brine (125 mL×3 times), 1M hydrochloric acid (125 mL) and water (125 mL), and concentrated under reduced pressure until the weight became 75 g or less. To the residue was added toluene (188 mL) and the mixture was concentrated again under reduced pressure. Toluene (about 500 mL) was added to give a toluene solution (481 g) of the title compound. The whole amount of the obtained toluene solution was used as total yield 100% in the following Step 5.

$^1$H-NMR (400 MHz, DMSO-D$_6$) δ: 8.17 (dd, 1H, J=8.32, 0.92 Hz), 7.66-7.60 (m, 2H), 7.40-7.34 (m, 1H), 7.29 (d, 1H, J=2.3 Hz), 7.16 (d, 1H, J=2.3 Hz), 4.12 (s, 1H), 4.18 (t, 2H, J=7.2 Hz), 1.85 (t, 2H, J=7.2 Hz), 1.18 (s, 6H).

Step 5

(9R)-4-Bromo-2-(3-hydroxy-3-methylbutyloxy)-9-(trifluoromethyl)-9H-fluoren-9-ol hemimethanol solvate (Compound (2 m))

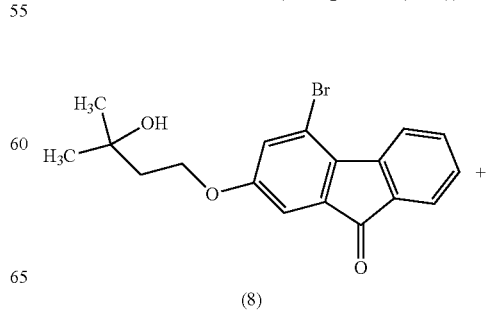

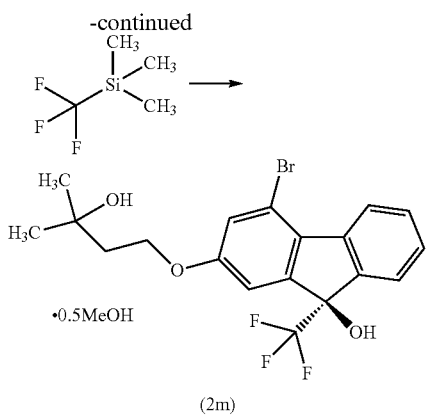

(2m)

Under a nitrogen atmosphere, to a toluene solution (481 g) of 4-bromo-2-(3-hydroxy-3-methylbutyloxy)-9H-fluoren-9-one (compound (8)) obtained in the previous step were added N-(4-tert-butyl-3-methoxybenzyl)cinchonidium bromide (compound (15)) (2.49 g), sodium phenolate (524 mg) and tetrahydrofuran (130 mL), the mixture was cooled, and (trifluoromethyl)trimethylsilane (11.4 g) was added dropwise over 3 min at an inside temperature of −52 to −51° C. The obtained mixture was stirred at an inside temperature of −52 to −48° C. for 30 min, the temperature was raised to about 0° C. over 1 hr, and cooled again to an inside temperature of −53° C. To the reaction mixture was added dropwise (trifluoromethyl)trimethylsilane (19.2 g) at an inside temperature of −53 to −47° C. over 2 hr, and the mixture was stirred at an inside temperature of about −50° C. for 10 min. The temperature of the obtained reaction mixture was raised to room temperature and the reaction mixture was concentrated under reduced pressure until the weight became 81.5 g or less, and methanol (130 mL) was added. To the obtained methanol solution was added dropwise 1M hydrochloric acid (32.6 mL) at room temperature and the mixture was stirred for 3 hr. The obtained reaction mixture was concentrated under reduced pressure until the weight became 97.8 g or less. Toluene (293 mL) and 10% brine (163 mL) were added to the mixture and the mixture was partitioned, and the aqueous layer was removed. The obtained organic layer was washed with water (163 mL) and concentrated under reduced pressure until the weight became 97.8 g or less. To the obtained concentrate was added methanol (163 mL) and the mixture was concentrated again under reduced pressure until the weight became 97.8 g or less, and methanol (163 mL) and activated carbon (4.89 g) were added. The obtained mixture was stirred at room temperature for 3 hr, filtered and the residue was washed with methanol (98 mL). The obtained filtrate and washing were concentrated under reduced pressure until the weight became 97.8 g or less, and methanol was added to give a methanol solution (130 g). To the obtained methanol solution was added water (57 mL) at an inside temperature of about 50° C. and a seed crystal (33 mg) of (9R)-4-bromo-2-(3-hydroxy-3-methylbutyloxy)-9-(trifluoromethyl)-9H-fluoren-9-ol hemimethanol solvate (compound (2m)) was added at an inside temperature of 45° C. The obtained suspension was stirred at an inside temperature of about 45° C. for 2 hr, cooled to room temperature and stirred overnight. The precipitated solid was collected by filtration, and washed with a methanol/water (1.3 v/0.7 v) mixed solution (65 mL) cooled to 10° C. or below. The obtained solid was dried under reduced pressure to give the title compound (23.9 g).

$^1$H-NMR (400 MHz, DMSO-D$_6$) δ: 8.31 (ddd, 1H, J=7.8, 1.2, 0.7 Hz), 7.65 (dddd, 1H, J=7.8, 1.4, 0.9, 0.7 Hz), 7.54 (ddd, 1H, J=7.6, 7.6, 1.4 Hz), 7.40 (ddd, 1H, J=7.6, 7.6, 1.2 Hz), 7.40 (s, 1H), 7.29 (d, 1H, J=2.3 Hz), 7.19 (dd, 1H, J=2.3, 0.9 Hz), 4.42 (s, 1H), 4.18 (t, 2H, J=7.2 Hz), 4.08 (q, 0.49H, J=5.4 Hz), 3.17 (d, 1.42H, J=5.4 Hz), 1.86 (t, 2H, J=7.2 Hz), 1.18 (s, 6H).

(Thermogravimetric Analysis)

The weight decrease by thermogravimetric analysis was well consistent with the theoretical value of compound (2m) (hemimethanol solvate of compound (2)).

Calculated: 3.58% (calculated value as hemimethanol solvate)

Found: 3.56%.

Synthesis of Seed Crystal of Compound (2m):

After the treatment with 1M hydrochloric acid in Step 5, concentration under reduced pressure, toluene-10% brine partitioning and washing with water gave a toluene solution. The toluene solution was concentrated and compound (2) was isolated (optical purity 70.5% e.e.) by silica gel column chromatography (eluent: hexane/ethyl acetate (3 v/2 v) to (5 v/4 v)). The isolated compound (2) was crystallized from an MeOH/water (3 v/1.7 v) mixed solution to give a seed crystal of compound (2m) (optical purity 98.9% e.e.). The optical purity was determined under HPLC analysis condition 3. The retention time of (R) form was 24.5 min, and the retention time of (S) form was 23.2 min.

Step 6

(9R)-4-Bromo-2-(3-hydroxy-3-methylbutyloxy)-9-(trifluoromethyl)-9H-fluoren-9-ol (Compound (2))

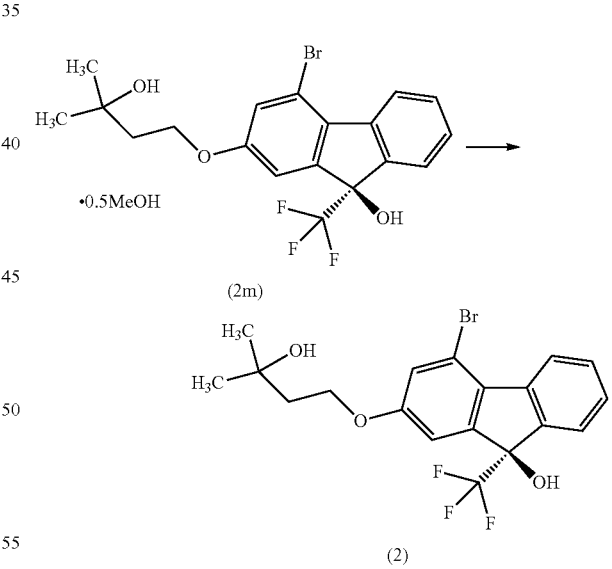

Under a nitrogen atmosphere, to (9R)-4-bromo-2-(3-hydroxy-3-methylbutyloxy)-9-(trifluoromethyl)-9H-fluoren-9-ol hemimethanol solvate (compound (2m)) (23.9 g) obtained in the previous step was added n-heptane (120 mL), the obtained suspension was stirred for 1 hr while maintaining an inside temperature of 85° C. or over, and about 25 mL of the solvent was removed under reduced pressure while maintaining an inside temperature of about 70° C. To the obtained suspension was added n-heptane (25 mL) at an inside temperature of about 70° C., and about 25 mL of the solvent was removed again under reduced pressure while maintaining an inside temperature of about 70° C. To the obtained suspension was added n-heptane (25 mL) at an inside temperature of about 70° C. and, after cooling to room temperature, the mixture was stirred for about 2 hr. The solid was collected by filtration and washed with n-heptane. The obtained solid was dried under reduced pressure at an outer temperature of 60° C. to give the title compound (22.2 g, optical purity 99.1% e.e.). The optical purity was determined under HPLC analysis condition 3. The retention time of (R) form was 24.5 min, and the retention time of (S) form was 23.2 min. The specific optical rotation was $[\alpha]_D$ +11.4° (c=1.00 MeOH 25° C.).

$^1$H-NMR (DMSO-D$_6$) δ: 8.30 (ddd, 1H, J=7.8, 1.2, 0.7 Hz), 7.64 (dddd, 1H, J=7.8, 1.4, 0.9, 0.7 Hz), 7.53 (ddd, 1H, J=7.6, 7.6, 1.4 Hz), 7.39 (ddd, 1H, J=7.6, 7.6, 1.2 Hz), 7.39 (s, 1H), 7.28 (d, 1H, J=2.3 Hz), 7.18 (dd, 1H, J=2.3, 0.9 Hz), 4.41 (s, 1H), 4.16 (t, 2H, J=7.2 Hz), 1.85 (t, 2H, J=7.2 Hz), 1.17 (s, 6H).

In addition, the absolute configuration of the single crystal of compound (2) obtained by recrystallization using heptane was determined by single crystal X-ray crystal analysis.

Compound (2) was derivatized to the below-mentioned compound (1h) and the specific optical rotation thereof was measured. As a result, specific optical rotation equivalent to that of a compound (2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropanamidemonohydrate described in WO 2014/142290 (compound (2h) described in WO 2014/142290)) was shown.

Step 7

Tert-butyl 2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropionate (Compound (4))

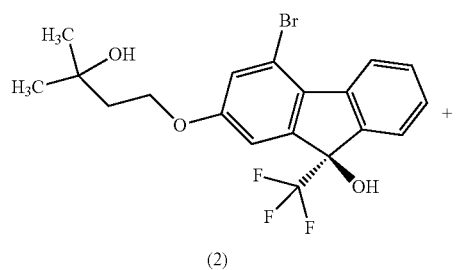

(2)

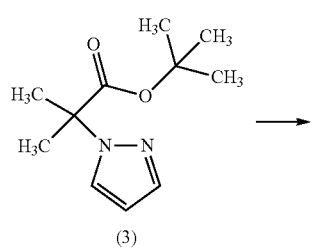

(3)

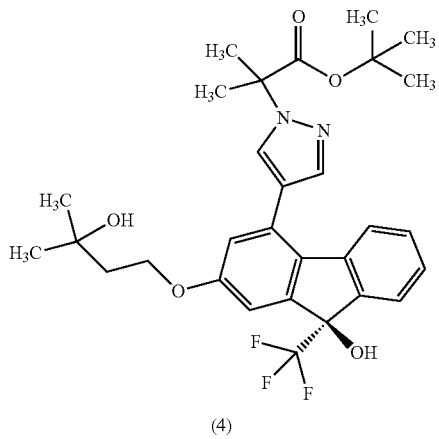

(4)

Under a nitrogen atmosphere, to bis(triphenylphosphine) palladium(II) dichloride (2.44 g) were added N,N-dimethylacetamide (420 mL), pivalic acid (3.55 g) and potassium carbonate (15.4 g). To the obtained mixture were added (9R)-4-bromo-2-(3-hydroxy-3-methylbutyloxy)-9-(trifluoromethyl)-9H-fluoren-9-ol (compound (2)) (60.0 g), tert-butyl 2-methyl-2-(1H-pyrazol-1-yl)propionate (compound (3)) (46.8 g) and N,N-dimethylacetamide (60 mL). The obtained mixture was stirred at 104 to 107° C. for 3 hr, the reaction mixture was concentrated under reduced pressure and about 440 mL of N,N-dimethylacetamide was evaporated. The obtained concentrate containing the title compound was used for the next step as yield 100%.

$^1$H-NMR (400 MHz, DMSO-D$_6$) δ: 8.16 (d, 1H, J=0.7 Hz), 7.68 (d, 1H, J=0.7 Hz), 7.62-7.57 (m, 1H), 7.32-7.18 (m, 3H), 7.23 (s, 1H), 7.15 (d, 1H, J=2.4 Hz), 6.84 (d, 1H, J=2.4 Hz), 4.41 (s, 1H), 4.16 (t, 2H, J=7.2 Hz), 1.87 (t, 2H, J=7.2 Hz), 1.81 (s, 6H), 1.38 (s, 9H), 1.18 (s, 6H).

Step 8

2-{4-[(9R)-9-Hydroxy-2-(3-hydroxy-3-methylbutyloxy)-9-(trifluoromethyl)-9H-fluoren-4-yl]-1H-pyrazol-1-yl}-2-methylpropionic acid (Compound (5))

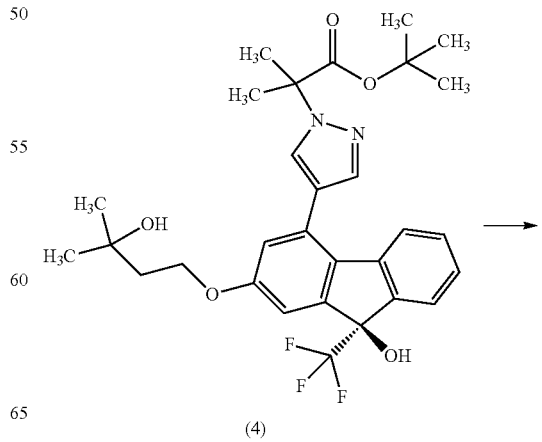

(4)

-continued

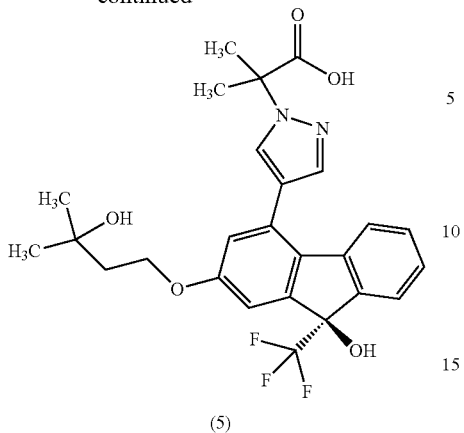

(5)

Under a nitrogen atmosphere, to a concentrate of tert-butyl 2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropionate (compound (4)) obtained in Step 7 were added activated carbon (6.00 g), 40% aqueous sodium hydroxide solution (120 mL) and ethanol (180 mL), and the mixture was stirred at an inside temperature of 70 to 73° C. for 1 hr 30 min. After cooling to room temperature, water (120 mL) was added, the obtained mixture was filtered through celite, and the residue was washed with an ethanol/water (1 v/1 v) mixed solution (180 mL). The obtained filtrate and washing were concentrated under reduced pressure until the weight became 428 g, toluene (480 mL) and water (180 mL) were added, and the mixture was partitioned at an inside temperature of 40 to 50° C. In a different vessel were added 85% phosphoric acid (228 g) and water (180 mL), the obtained aqueous phosphoric acid solution was cooled, and ethyl acetate (360 mL) was added at an inside temperature of about 0° C. To the obtained mixture was added dropwise the aqueous layer obtained by partitioning performed earlier at an inside temperature of −7 to 14° C. The mixture was partitioned and the aqueous layer was removed. The obtained organic layer was washed 4 times with water (300 mL), concentrated under reduced pressure until the weight became 135 g, ethyl acetate (300 mL) was added, and the mixture was concentrated again under reduced pressure until the liquid weight became 138 g. To the obtained concentrate were added ethyl acetate (420 mL) and activated carbon (3.00 g). The obtained mixture was stirred at an inside temperature of 23 to 26° C. for 2 hr 20 min, filtered, and the residue was washed with ethyl acetate (120 mL). The obtained filtrate and washing were concentrated under reduced pressure at an outer temperature of 50° C. until the weight became 150 g, ethyl acetate (300 mL) was added, and the mixture was concentrated again under reduced pressure at an outer temperature of 50° C. until the liquid weight became 150 g. The obtained solution was stirred at an inside temperature of 45 to 50° C. for 1 hr 30 min and precipitation of crystals was confirmed. To the obtained suspension was added dropwise toluene (390 mL) at an inside temperature of 46 to 49° C., and the mixture was stirred at an inside temperature of 47 to 52° C. for 1 hr 10 min, cooled to room temperature and stirred overnight. The precipitated solid was collected by filtration, and washed with a toluene/ethyl acetate (7 v/1 v) mixed solution (120 mL). The obtained solid was dried under reduced pressure to give the title compound (58.9 g).

$^1$H-NMR (400 MHz, DMSO-D$_6$) δ: 13.09 (brs, 1H), 8.17 (d, 1H, J=0 0.6 Hz), 7.64 (d, 1H, J=0.6 Hz), 7.61-7.56 (m, 1H), 7.29-7.18 (m, 4H), 7.15 (d, 1H, J=2.4 Hz), 6.86 (d, 1H, J=2.4 Hz), 4.40 (s, 1H), 4.16 (t, 2H, J=7.2 Hz), 1.87 (t, 2H, J=7.2 Hz), 1.84 (s, 3H), 1.83 (s, 3H), 1.18 (s, 6H).

Step 9

2-{4-[(9R)-9-Hydroxy-2-(3-hydroxy-3-methylbutyloxy)-9-(trifluoromethyl)-9H-fluoren-4-yl]-1H-pyrazol-1-yl}-2-methylpropanamide monohydrate (Compound (1h))

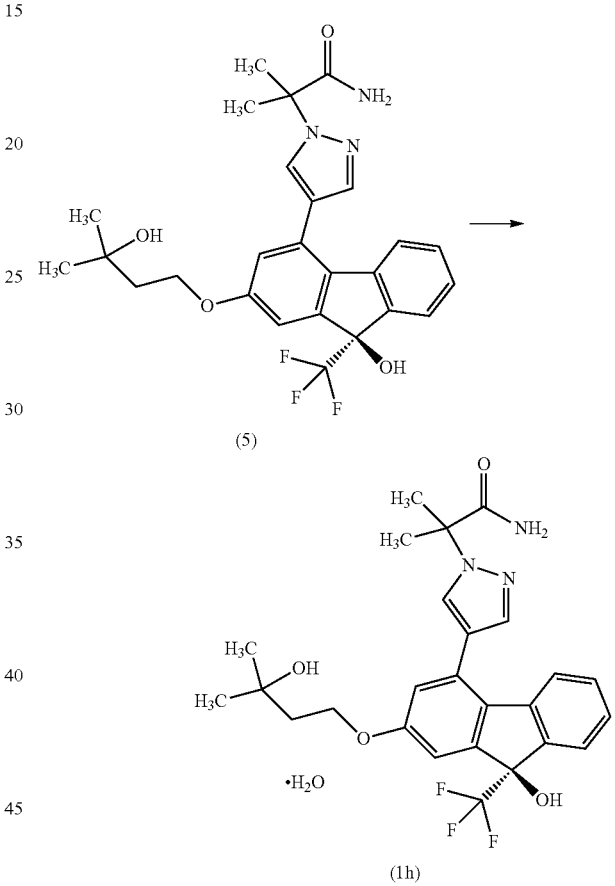

Under a nitrogen atmosphere, 2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropionic acid (compound (5)) (58.0 g) and 1-hydroxybenzotriazole monohydrate (17.6 g) were dissolved in N,N-dimethylformamide (174 mL). The obtained solution was cooled to 4° C. and 28% aqueous ammonia solution (11.6 mL) was added dropwise while maintaining an inside temperature of less than 15° C. To the obtained solution was added 1-ethyl-3-(3-dimethylaminopropyl)carbodiimide hydrochloride (6.60 g) at room temperature, and the mixture was stirred at room temperature for 1 hr 40 min. Successively, at room temperature, 1-ethyl-3-(3-dimethylaminopropyl)carbodiimide hydrochloride (6.60 g) was added and the mixture was stirred at room temperature for about 1 hr 30 min. This operation was repeated 3 times. To the obtained reaction mixture were added ethyl acetate (580 mL), 20% brine (232 mL) and water (58 mL) for partitioning and the aqueous layer was removed. The obtained organic layer was washed by adding ethyl acetate (116 mL) and 5% aqueous sodium hydrogen carbonate solution (290 mL). Subsequently, the organic layer was washed successively with water (116 mL), 1M hydrochloric acid (290 mL), 5% brine (290 mL) and water (290 mL), and the obtained organic layer was concentrated under reduced pressure until the weight became 121 g. To the obtained concentrate was added ethanol (174 mL), and the mixture was concentrated under reduced pressure until the weight became 109 g. Ethanol (174 mL) was added and the mixture was concentrated again under reduced pressure until the weight became 112 g. To the obtained concentration liquid was added ethanol (93 mL) and the liquid amount was adjusted to 200 mL. The obtained solution was filtered to remove dust, and the residue was washed with ethanol (116 mL). The obtained filtrate and washing were heated, water (348 mL) was added dropwise thereto at an inside temperature of 46 to 50° C., seed crystal (12 mg) was added, and the mixture was stirred at an inside temperature of 46 to 51° C. for 2 hr. The obtained suspension was further stirred at an inside temperature of 55 to 62° C. for 1 hr 10 min, cooled to 30° C. over about 4 hr and stirred at room temperature overnight. The precipitated solid was collected by filtration, successively washed with an ethanol/water (5 v/7 v) mixed solution (116 mL) and water (116 mL). The obtained solid was dried under reduced pressure at an outer temperature of 30° C., 1.3 kPa to give the title compound (54.6 g, optical purity>99.9% e.e.). The optical purity was determined under HPLC analysis condition 4. The retention time of (R) form was 6.4 min, and the retention time of (S) form was 9.2 min.

The specific optical rotation was $[\alpha]_D$ +39.1° (c=1.00 MeOH 25° C.). $^1$H-NMR (400 MHz, DMSO-D$_6$) δ: 8.09 (d, 1H, J=0.9 Hz), 7.68 (d, 1H, J=0.9 Hz), 7.62-7.56 (m, 1H), 7.36-7.30 (m, 1H), 7.30-7.22 (m, 3H), 7.21 (s, 1H), 7.14 (d, 1H, J=2.5 Hz), 6.97 (brs, 1H), 6.88 (d, 1H, J=2.5 Hz), 4.40 (s, 1H), 4.16 (t, 2H, J=7.2 Hz), 1.87 (t, 2H, J=7.2 Hz), 1.80 (s, 3H), 1.80 (s, 3H), 1.18 (s, 6H).

(Water Content Determination)

The quantitative value of water by Karl Fischer titration method (coulometric titration) was well consistent with the theoretical value of compound (1h) (monohydrate of compound (1)).

Calculated: 3.45% (calculated value as monohydrate).
Found: 3.48%.

Synthesis of Seed Crystal of Compound (1h):

The seed crystal used in Step 9 was produced from a mixed solvent of ethanol and water by using a solid obtained according to the Example (2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropanamide monohydrate/compound (2h)) described in WO 2014/142290.

Alternative to Step 9:

Even when seed crystal was not added at the time of crystallization, the crystal of the object compound (1h) was obtained by a method analogous to this Step 9.

Step 10

Synthesis of tert-butyl 2-methyl-2-(1H-pyrazol-1-yl)propionate (Compound (3))

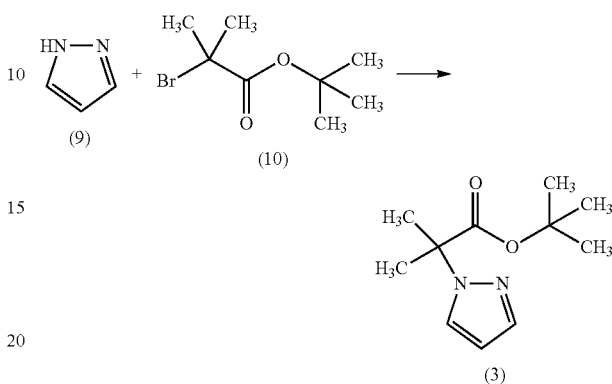

Under a nitrogen atmosphere, tetrahydrofuran (1250 mL) and 60% sodium hydride (58.5 g) were added, and was cooled to the inside temperature of −9° C. To the obtained suspension was added dropwise a pyrazole (compound (9)) (100 g)/tetrahydrofuran (250 mL) solution at an inside temperature of −9 to 5° C., and the mixture was stirred at −5 to 0° C. for 30 min. The temperature of the obtained mixture was raised to an inside temperature of 14° C., tert-butyl 2-bromo-2-methylpropionate (compound (10)) (377 g) was added at an inside temperature of 14 to 16° C., and the mixture was stirred at an inside temperature of 18° C. for 15 min and then stirred at an inside temperature of 47 to 51° C. for 11 hr. The obtained reaction mixture was cooled to an inside temperature of 1° C., a potassium tert-butoxide (82.3 g)/tetrahydrofuran (300 mL) solution was added dropwise at an inside temperature of 1 to 7° C., and the mixture was stirred at 10 to 12° C. for 5 hr. To the obtained reaction mixture were added toluene (800 mL) and water (800 mL) at room temperature for partitioning, and the aqueous layer was removed. The obtained organic layer was washed with 1M hydrochloric acid (800 mL) and water (400 mL×2 times) and concentrated under reduced pressure. The obtained concentrate was distilled under reduced pressure at an outer temperature of about 110° C., reduced pressure of about 0.6 kPa to give the title compound (229 g).

$^1$H-NMR (400 MHz, DMSO-D$_6$) δ: 7.83 (dd, 1H, J=2.4, 0.7 Hz), 7.46 (dd, 1H, J=1.8, 0.7 Hz), 6.26 (dd, 1H, J=2.4, 1.8 Hz), 1.71 (s, 6H), 1.32 (s, 9H).

INDUSTRIAL APPLICABILITY

The present invention can provide a method for producing the compound of the formula [I] or a pharmaceutically acceptable salt thereof, or a hydrate thereof in a good yield.

In addition, the compounds of the formula [II], the formula [IIm], the formula [III] and the formula [IV] of the present invention are useful as synthesis intermediates for producing the compound of the formula [I] or a pharmaceutically acceptable salt thereof, or a hydrate thereof.

Furthermore, the production method of the present invention is useful as a method for industrial large-scale synthesis since the method can be performed by a convenient operation via compounds easy to handle.

The invention claimed is:

1. A method for producing a compound represented by formula [I]:

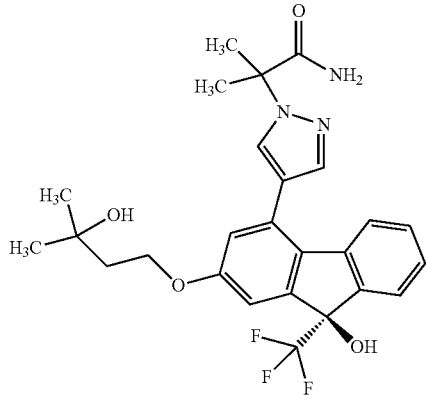

or a pharmaceutically acceptable salt thereof, or a hydrate thereof, wherein the method comprises a step of converting a compound represented by formula [II]:

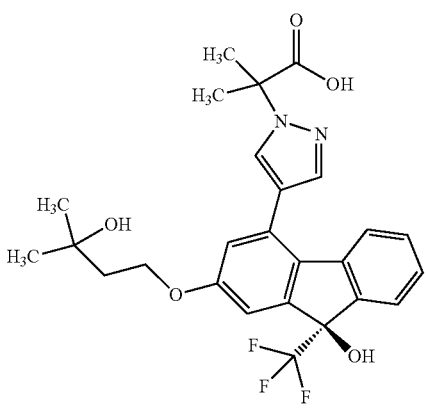

or a methanol solvate thereof, to a compound represented by formula [IV]:

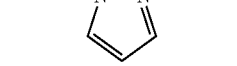

by a coupling reaction with a compound represented by formula [III]:

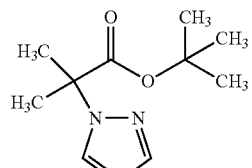

in the presence of a metal catalyst, a base and carboxylic acid.

2. The method according to claim 1, wherein the metal catalyst is a palladium catalyst.

3. The method according to claim 1, wherein the base is alkali metal carbonate or alkali metal acetate.

4. The method according to claim 1, wherein the carboxylic acid is pivalic acid, isobutyric acid, propionic acid or benzoic acid.

5. The method according to claim 1, wherein a reaction temperature of the coupling reaction is 80 to 150° C.

6. The method according to claim 1, further comprising a step of hydrolyzing the compound of formula [IV] to convert the compound of formula [IV] to a compound represented by formula [V]:

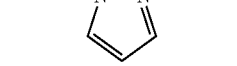

or a salt thereof.

7. The method according to claim 6, further comprising a step of reacting the compound of formula [V] or the salt thereof with ammonia in the presence of a condensing agent to convert the compound of formula [V] to the compound represented by formula [I] or the pharmaceutically acceptable salt thereof, or a hydrate thereof.

8. The method according to claim 1, wherein the compound of formula [II] is produced by a method comprising: a step of reacting a compound represented by formula [VI]:

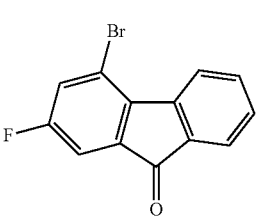

with a compound represented by formula [VII]:

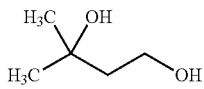

in the presence of a base to convert the compound of formula [VI] to a compound represented by formula [VIII]:

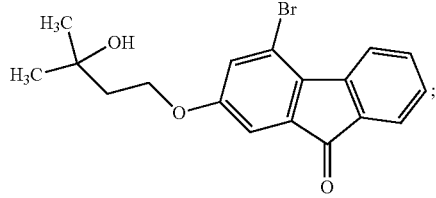

and a step of reacting the compound of formula [VIII] with (trifluoromethyl)trimethylsilane in the presence of an asymmetric organocatalyst and then treating with an acid.

9. The method according to claim 8, wherein the asymmetric organocatalyst is a cinchonidium salt.

10. The method according to claim 9, wherein the cinchonidium salt is N-(4-tert-butyl-3-methoxybenzyl)cinchonidium bromide.

11. The method according to claim 1, wherein the compound of formula [III] is produced by reacting a compound represented by the formula [IX]:

or a salt thereof with a compound represented by formula [X]:

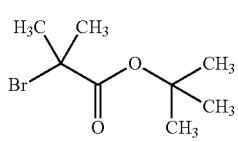

in the presence of a base.

12. A method for producing a compound represented by formula [I]:

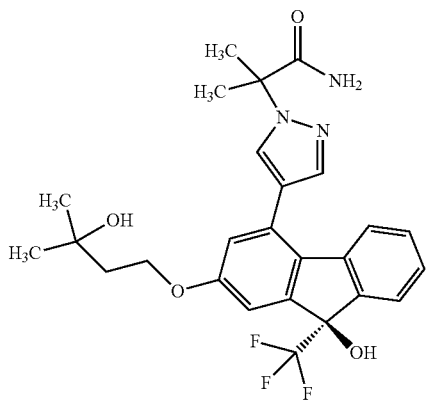

or a pharmaceutically acceptable salt thereof, or a hydrate thereof, wherein the method comprises a step of reacting a compound represented by formula [VI]:

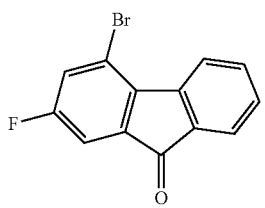

with a compound represented by formula [VII]:

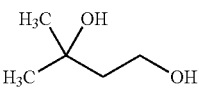

in the presence of a base to convert the compound of formula [VI] to a compound represented by formula [VIII]:

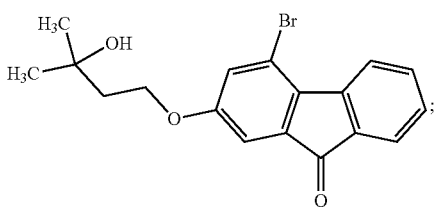

a step of reacting the compound of formula [VIII] with (trifluoromethyl)trimethylsilane in the presence of an asymmetric organocatalyst and then treating with an acid to give a compound represented by formula [II]:

[II]

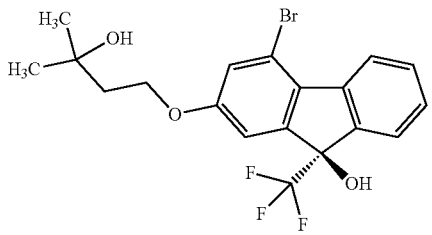

or a methanol solvate thereof;
a step of reacting a compound represented by formula [IX]:

[IX]

or a salt thereof with a compound represented by formula [X]:

[X]

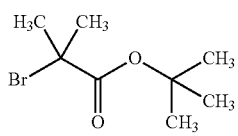

in the presence of a base to give a compound represented by formula [III]:

[III]

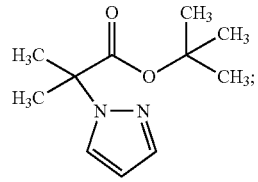

a step of subjecting the compound of formula [III] to a coupling reaction with the compound of formula [II] or the methanol solvate thereof in the presence of a metal catalyst, a base and carboxylic acid to convert the compound of formula [II] to a compound represented by formula [IV]:

[IV]

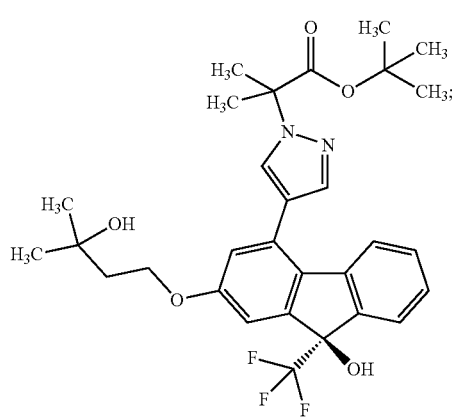

a step of hydrolyzing the compound of formula [IV] to convert the compound of formula [IV] to a compound represented by formula [V]:

[V]

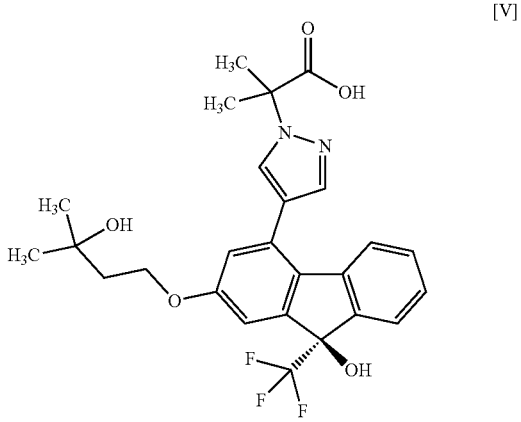 [SMILES: CC(C)(O)CCOc1cc(-c2cnn(C(C)(C)C(=O)O)c2)c2c(c1)[C@@](O)(C(F)(F)F)c1ccccc1-2]

or a salt thereof; and
a step of amidating the compound of formula [V] or the salt thereof by reacting with ammonia in the presence of a condensing agent.

13. A method for producing a compound represented by formula [IV]:

[IV]

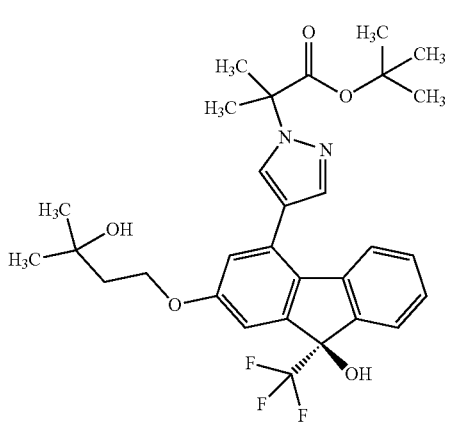

comprising subjecting a compound represented by formula [II]:

[II]

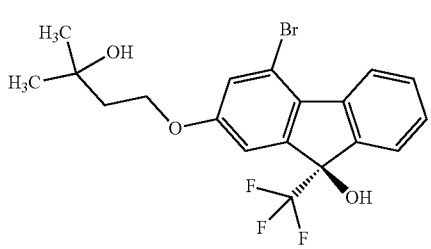

or a methanol solvate thereof to a coupling reaction with a compound represented by formula [III]:

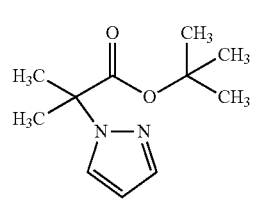
[III]
in the presence of a metal catalyst, a base and carboxylic acid.
* * * * *